US007112585B2

(12) United States Patent
Hartz et al.

(10) Patent No.: US 7,112,585 B2
(45) Date of Patent: Sep. 26, 2006

(54) PYRIMIDINE DERIVATIVES AS CORTICOTROPIN RELEASING FACTOR INHIBITORS

(75) Inventors: Richard A. Hartz, Middletown, CT (US); Argyrios G. Arvanitis, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 306 days.

(21) Appl. No.: 10/800,241

(22) Filed: Mar. 12, 2004

(65) Prior Publication Data

US 2004/0229891 A1 Nov. 18, 2004

Related U.S. Application Data

(60) Provisional application No. 60/464,063, filed on Apr. 18, 2003.

(51) Int. Cl.
*C07D 401/12* (2006.01)
*C07D 239/47* (2006.01)
*A61K 31/506* (2006.01)
*C07D 239/38* (2006.01)

(52) U.S. Cl. .............. 514/235.8; 514/252.14; 514/269; 544/122; 544/296; 544/298

(58) Field of Classification Search .......... 544/122, 544/296, 298; 514/235.8, 269, 252.14
See application file for complete search history.

(56) References Cited

FOREIGN PATENT DOCUMENTS

| WO | WO 95/10506 | 4/1995 |
|---|---|---|
| WO | WO 95/33750 | 12/1995 |
| WO | WO 97/45421 | 12/1997 |
| WO | WO 98/03510 | 1/1998 |
| WO | WO 99/51608 | 10/1999 |
| WO | WO 00/53604 | 9/2000 |
| WO | WO 00/59888 | 10/2000 |
| WO | WO 01/53263 A1 | 7/2001 |
| WO | WO 01/62718 | 8/2001 |
| WO | WO 01/68614 A2 | 9/2001 |
| WO | WO 02/06242 A2 | 1/2002 |

OTHER PUBLICATIONS

Ulrich, Crystallization, Kirk-Othmer Encyclopedia of Chemical Technology, vol. 8, pp. 113-120, (http://www.mrw.interscience.wiley.com/kirk/articles/crysrous.a01/sect4-fs.html) Aug. 2002.*
West, Solid Solutions, Solid state chemistry and it's applications, Wiley, New York, pp. 358 and 365, 1988.*
Vippagunta et al., Crystalline solids, Advanced Drug Delivery Reviews, 48 (2001), pp. 3-26, 2001.*
Dunn, A.J., et al., "Physiological and behavioral responses to corticotropin-releasing factor administration: is CRF a mediator of anxiety or stress responses?" Brain Research Reviews, 15, 1990, pp. 71-100.

Gulyas, J, et al., "Potent structurally constrained agonists and competitive antagonists of corticotropin-releasing factor," Proc. Natl. Acad. Sci. USA, vol. 92, Nov. 1995, pp. 10575-10579.
McCarthy, et al., "Recent Advances with the CRF1 Receptor: Design of Small Molecule Inhibitors, Receptor Subtypes and Clinical Indications," Current Pharmaceutical Design, 1999, 5, pp. 289-315.
Holsboer, F., "The rationale for corticotropin-releasing hormone receptor (CRH-R) antagonists to treat depression and anxiety," Journal of Psychiatric Research, 33, 1999, pp. 181-214.
Banki, C.M., et al., "CSF corticotropin-releasing hormone and somatostatin in major depression: response to antidepressant treatment and relapse," European Neuropsychopharmacology, 2, 1992, pp. 107-113.
Webster, E.L., et al., "Corticotropin-Releasing Hormone and Inflammation," Annals New York Academy of Sciences, 840, 1998, pp. 21-32.
Gilligan, P.J., et al., "Corticotropin Releasing Factor (CRF) Receptor Modulators: Progress and Opportunities for New Therapeutic Agents," Journal of Medicinal Chemistry, vol. 43, No. 9, May 4, 2000, pp. 1641-1660.
McCarthy, J.R., et al., "Chapter 2. Recent Progress in Corticotropin-Releasing Factor Receptor Agents," Annual Reports in Medicinal Chemistry, vol. 34, 1999, pp. 11-20.

* cited by examiner

*Primary Examiner*—Deepak Rao
(74) *Attorney, Agent, or Firm*—Shah R. Makujina; James R. Epperson

(57) ABSTRACT

The present invention relates to novel heterocyclic antagonists of Formula (I) and pharmaceutical compositions comprising said antagonists of the corticotropin releasing factor receptor ("CRF receptor")

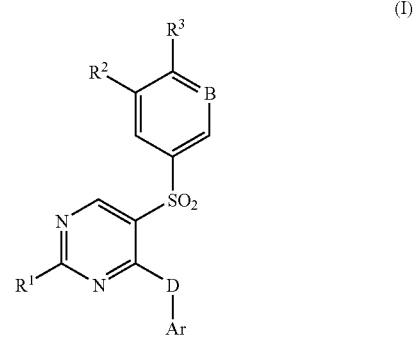

useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

16 Claims, No Drawings

US 7,112,585 B2

PYRIMIDINE DERIVATIVES AS CORTICOTROPIN RELEASING FACTOR INHIBITORS

CROSS REFERENCE TO RELATED APPLICATION

This non-provisional application claims priority from provisional application U.S. Ser. No. 60/464,063 filed Apr. 18, 2003. The disclosure of this prior application is incorporated herein by reference in its entirety.

FIELD OF THE INVENTION

The present invention relates to antagonists and pharmaceutical compositions comprising said antagonists of the corticotropin releasing factor receptor ("CRF receptor") useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

BACKGROUND OF THE INVENTION

It has been shown that the neuropeptide, corticotropin releasing factor ("CRF"), acting through its binding to the CRF-1 receptor, is a primary mediator of stress- and anxiety-related physiological responses in humans and other mammals by stimulating ACTH secretion from the anterior pituitary gland. See A. J. Dunn, et al., *Brain Res. Rev.*, 15: 71–100 (1990). Antagonists of the CRF-1 receptor, both peptides (J. Gulyas, et al., *Proc. Natl. Acad. Sci. U.S.A.*, 92: 10575–10579 (1995) and small molecules (J. R. McCarthy, et al., *Curr. Pharm. Design*, 5: 289–315 (1999), have demonstrated the ability to ameliorate the effects of stressful stimuli in several animal models. In addition, marked elevations of CRF in cerebrospinal fluid have been detected in a large portion of individuals diagnosed with major depression and anxiety disorders, and the levels correlate with severity of the disease. See F. Holsboer, *J. Psychiatric Res.*, 33: 181–214 (1999). Following antidepressant treatment, the increased CRF levels observed in depressed patients were reduced. See C. M. Banki, et al., *Eur. Neuropsychopharmacol.*, 2: 107–113 (1992). CRF has also been shown to be a key mediator of several immune system functions through its effect on glucocorticoid plasma levels. See E. L. Webster, et al., *Ann. N.Y. Acad. Sci.*, 840: 21–32 (1998). Recent reviews of the activity of CRF-1 antagonists, P. J. Gilligan, et al., *J. Med. Chem.*, 43: 1641–1660 (2000) and J. R. McCarthy, et al., *Ann. Rep. Med. Chem.*, 34: 11–20 (1999) are incorporated herein by reference. There appears a need to discover novel small molecule CRF antagonists in order to treat a wide variety of human disorders including depression, anxiety, bipolar disorder, and other stress-related illnesses. See WO 95/10506, WO 95/33750, WO 97/45421, WO 98/03510, WO 99/51608, WO 00/59888, WO 00/53604, WO 01/53263, WO 01/62718, WO 01/68614, WO 02/06242 and PCT/US99/18707.

SUMMARY OF THE INVENTION

Thus according to a first embodiment of the first aspect of the present invention are provided compounds of Formula (I)

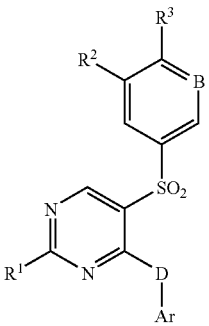

or pharmaceutically acceptable salts or solvates thereof, wherein

B is CH or N;

D is $CH_2$ or NH;

$R^1$ is selected from the group consisting of H, —CN, $C_{1-4}$ alkyl, $C_{3-7}$ cycloalkyl, $C_{2-4}$ alkenyl, $C_{2-4}$ alkynyl, $C_{1-4}$ alkoxy and $N(C_{1-4}$ alkyl$)_2$ optionally and independently substituted with 1 to 3 substituents selected from the group consisting of —CN, hydroxy, halo, $C_{1-4}$ haloalkyl and $C_{1-4}$ alkoxy;

$R^2$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —$NR^4R^6$, —$C_{1-6}$alkyl$NR^4R^6$, —$C_{1-6}$alkyl$OR^6$, $CO_2R^6$, $O_2CR^6$, $COR^6$, $CON^4R^6$, $NR^4CO_2R^6$, $NR^4SO_2R^6$, $NR^4COR^6$, $OCONR^4R^6$ and $NR^4CONR^5R^6$;

optionally and independently substituted with 1 to 3 substituents selected from the group consisting of —CN, hydroxy, halo, $C_{1-4}$ haloalkyl, $C_{1-4}$ alkoxy, $CO_2C_{1-4}$ alkyl or phenyl; or $R^2$ is morpholinyl, thiomorpholinyl, piperadinyl, piperazinyl, phenyl, pyridyl, pyrimidinyl, triazinyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl and indazolyl, independently and optionally substituted with 1 to 4 substituents selected from the group consisting of H, $C_{1-6}$ alkyl, $C_{1-4}$ alkoxy-$C_{1-4}$ alkyl, $C_{3-6}$ cycloalkyl, —$OR^4$, halo, $C_{1-4}$ haloalkyl, —CN, SH, —$S(O)_2R^5$, —$COR^4$, —$CO_2R^4$, —$OC(O)R^5$, —$N(COR^4)_2$, —$NR^4R^7$ and —$CONR^4R^7$, —$NR^4COR^5$, $NR^4SO_2R^5$, $NR^4CONR^5R^7$ or $NR^4CO_2R^5$;

$R^3$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —$NR^4R^6$, —$C_{1-6}$alkyl$NR^4R^6$, —$C_{1-6}$alkyl$OR^6$, $CO_2R^6$, $O_2CR^6$, $COR^6$, $CON^4R^6$, $NR^4CO_2R^6$, $NR^4SO_2R^6$, $NR^4COR^6$, $OCONR^4R^6$, and $NR^4CONR^5R^6$;

optionally and independently substituted with 1 to 3 substituents selected from the group consisting of —CN, hydroxy, halo, $C_{1-4}$ haloalkyl, $C_{1-4}$ alkoxy, $CO_2C_{1-4}$ alkyl, phenyl or naphthl; or $R^3$ is morpholinyl, thiomorpholinyl, piperadinyl, piperazinyl, phenyl, pyridyl, pyrimidinyl, triazinyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl and indazolyl, independently and optionally substituted with 1 to 4 substituents selected from the group consisting of H, $C_{1-6}$ alkyl, $C_{3-6}$ cycloalkyl, $C_{1-4}$ alkoxy-$C_{1-4}$ alkyl, —$OR^4$, halo, $C_{1-4}$ haloalkyl, —CN, SH, —$S(O)_2R^5$, —$COR^4$, —$O_2R^4$, —$OC(O)R^5$, —$N(COR^4)_2$, —$NR^4R^7$ and —$CONR^4R^7$, —$NR^4COR^5$, $NR^4SO_2R^5$, $NR^4CONR^5R^7$ or $NR^4CO_2R^5$;

Ar is selected from the group consisting of phenyl, indanyl, indenyl, pyridyl, pyrimidinyl, triazinyl, furanyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl, indazolyl, indolinyl, benzoxazolin-2-on-yl, benzodioxolanyl and benzodioxane, independently and optionally substituted with 1 to 4 substituents selected from the group consisting of H, $C_{1-6}$ alkyl, $C_{3-6}$ cycloalkyl, $C_{1-4}$ alkoxy-$C_{1-4}$ alkyl, —$OR^4$, halo, $C_{1-4}$ haloalkyl, —CN, —$NO_2$, SH, —$S(O)_2R^5$, —$COR^4$, —$CO_2R^4$, —$OC(O)R^5$, —$N(COR^4)_2$, —$NR^4R^7$ and —$CONR^4R^7$, —$NR^4COR^5$, $NR^4SO_2R^5$, $NR^4CONR^5R^7$, and $NR^4CO_2R^5$;

$R^4$, $R^5$ and $R^7$ are independently selected from the group consisting of H, $C_{1-6}$ alkyl, $C_{3-6}$ cycloalkyl, $C_{3-6}$ cycloalkyl-$C_{3-6}$ alkyl, $C_{1-2}$ alkoxy-$C_{1-4}$ alkyl and $C_{1-4}$ haloalkyl; and $R^6$ is selected from the group consisting of H, $C_{1-6}$ alkyl, $C_{3-6}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, phenyl and $C_{1-6}$ alkyl-phenyl.

According to another embodiment of the first aspect of the present invention are provided compounds of Formula (I) according to the first embodiment of the first aspect wherein B is CH.

According to another embodiment of the first aspect of the present invention are provided compounds of Formula (I) according to the first embodiment of the first aspect wherein B is CH and D is $CH_2$.

According to another embodiment of the first aspect of the present invention are provided compounds of Formula (I) according to the first embodiment of the first aspect wherein B is CH and D is NH.

According to another embodiment of the first aspect of the present invention are provided compounds of Formula (I) according to the first embodiment of the first aspect wherein $R^1$ is $C_{1-4}$ alkyl.

According to another embodiment of the first aspect of the present invention are provided compounds of Formula (I) according to the first embodiment of the first aspect wherein $R^2$ is H or substituted or unsubsituted $C_{1-6}$alkyl, morpholinyl, piperazinyl or phenyl.

According to another embodiment of the first aspect of the present invention are provided compounds of Formula (I) according to the first embodiment of the first aspect wherein $R^3$ is H, halo, CN or hydroxy, substituted or unsubstituted $C_{1-6}$ alkyl, $C_{1-6}$ alkoxy, $C_{1-6}$ haloalkyl, —$NR^4R^6$ or $O_2CR^6$.

According to another embodiment of the first aspect of the present invention are provided compounds of Formula (I) according to the first embodiment of the first aspect wherein $R^3$ is pyrimidinyl and pyridinyl.

According to another embodiment of the first aspect of the present invention are provided compounds of Formula (I) according to the first embodiment of the first aspect wherein Ar is phenyl, pyridyl, pyrimidinyl, imidazolyl, thiazolyl, pyrrolidinyl, dihydroimidazolyl optionally substituted with 1 to 4 substituents selected from the group consisting of H, $C^{1-6}$ alkyl, —$OR^4$, halo, $C_{1-4}$ haloalkyl, —CN, —$NO_2$ or —$CO_2R^4$.

According to another embodiment of the first aspect of the present invention are provided compounds of Formula (I) according to the first embodiment of the first aspect wherein $R^4$, $R^5$ and $R^7$ are independently H or $C_{1-6}$ alkyl.

According to another embodiment of the first aspect of the present invention are provided compounds of Formula (I) according to the first embodiment of the first aspect wherein $R^6$ is H.

According to another embodiment of the first aspect of the present invention are provided compounds of Formula (I) according to the first embodiment of the first aspect wherein $R^1$ is $C_{1-4}$ alkyl; $R^2$ is H or substituted or unsubsituted $C_{1-6}$alkyl, morpholinyl, piperazinyl or phenyl; $R^3$ is H, halo, CN or hydroxy, substituted or unsubstituted $C_{1-6}$ alkyl, $C_{1-6}$ alkoxy, $C_{1-6}$ haloalkyl, —$NR^4R^6$ or $O_2CR^6$; Ar is phenyl, pyridyl, pyrimidinyl, imidazolyl, thiazolyl, pyrrolidinyl, dihydroimidazolyl optionally substituted with 1 to 4 substituents selected from the group consisting of H, $C_{1-6}$ alkyl, —$OR^4$, halo, $C_{1-4}$ haloalkyl, —CN, —$NO_2$ or —$CO_2R^4$; $R^4$ $R^5$ and $R^7$ are independently H or $C_{1-6}$ alkyl; and $R^6$ is H.

According to another embodiment of the first aspect of the present invention are provided compounds of Formula (I) according to the first embodiment of the first aspect wherein B is CH; $R^1$ is $C_{1-4}$ alkyl; $R^2$ is H or substituted or unsubsituted $C_{1-6}$alkyl, morpholinyl, piperazinyl or phenyl; $R^3$ is H, halo, CN or hydroxy, substituted or unsubstituted $C_{1-6}$ alkyl, $C_{1-6}$ alkoxy, $C_{1-6}$ haloalkyl, —$NR^4R^6$ or $O_2CR^6$; Ar is phenyl, pyridyl, pyrimidinyl, imidazolyl, thiazolyl, pyrrolidinyl, dihydroimidazolyl optionally substituted with 1 to 4 substituents selected from the group consisting of H, $C_{1-6}$ alkyl, —$OR^4$, halo, $C_{1-4}$ haloalkyl, —CN, —$NO_2$ or —$CO_2R^4$; $R^4$ $R^5$ and $R^7$ are independently H or $C_{1-6}$ alkyl; and $R^6$ is H.

According to another embodiment of the first embodiment of the aspect of the present invention are provided compounds selected from the group consisting of [5-(4-Methoxybenzenesulfonyl)-2-methylpyrimidin-4-yl]-(2,4,6-trimethylphenyl)-amine; 4-[2-Methyl-4-(2,4,6-trimethylphenylamino)-pyrimidine-5-sulfonyl]-phenol; Acetic acid 4-[2-methyl-4-(2,4,6-trimethylphenylamino)-pyrimidine-5-sulfonyl]-phenyl ester; [5-(4-Benzyloxybenzenesulfonyl)-2-methylpyrimidin-4-yl]-(2,4,6-trimethylphenyl)-amine; [5-(4-Benzyloxybenzenesulfonyl)-2-methylpyrimidin-4-yl]-(4-methoxy-2-methylphenyl)-amine; [5-(4-Benzyloxybenzenesulfonyl)-2-methylpyrimidin-4-yl]-(6-methoxy-2-methylpyridin-3-yl)-amine; [5-(3-Benzyloxybenzenesulfonyl)-2-methylpyrimidin-4-yl]-(2,4,6-trimethylphenyl)-amine; [5-(3-Benzyloxybenzenesulfonyl)-2-methoxypyrimidin-4-yl]-(2,4,6-trimethylphenyl)-amine; 5-(3-Benzyloxybenzenesulfonyl)-$N^2$,$N^2$-dimethyl-$N^4$-(2,4,6-trimethylphenyl)-pyrimidine-2,4-diamine; {5-[4-(2-Methoxybenzyloxy)-benzenesulfonyl]-2-methylpyrimidin-4-yl}-(2,4,6-trimethylphenyl)-amine; {5-[4-(3,5-Dimethoxybenzyloxy)-benzenesulfonyl]-2-methylpyrimidin-4-yl}-(2,4,6-trimethylphenyl)-amine; [5-(4-Benzyloxybenzenesulfonyl)-2-methylpyrimidin-4-yl]-(2,4-dimethoxyphenyl)-amine; 5-(4-Methoxyoxybenzenesulfonyl)-2-methyl-4-(2,4,6-trimethylbenzyl)-pyrimidine; 5-(4-Benzyloxybenzenesulfonyl)-2-methyl-4-(2,4,6-trimethylbenzyl)-pyrimidine; [5-(4-Fluorobenzenesulfonyl)-2-methylpyrimidin-4-yl]-(2,4,6-trimethylphenyl)-amine; [2-Methyl-5-(4-morpholin-4-ylbenzenesulfonyl)-pyrimidin-4-yl]-(2,4,6-trimethylphenyl)-amine; {2-Methyl-5-[4-(4-methylpiperazin-1-yl)-benzenesulfonyl]-pyrimidin-4-yl}-(2,4,6-trimethylphenyl)-amine; [5-(4-Imidazol-1-yl-benzenesulfonyl)-2-methylpyrimidin-4-yl]-(2,4,6-trimethylphenyl)-amine; [2-Methyl-5-(4-pyrrolidin-1-yl-benzenesulfonyl)-pyrimidin-4-yl]-(2,4,6-trimethylphenyl)-amine; [5-(4-Benzylaminobenzenesulfonyl)-2-methylpyrimidin-4-yl]-(2,4,6-trimethylphenyl)-amine; {5-[4-(Benzylmethylamino)-benzenesulfonyl]-2-methylpyrimidin-4-yl}-(2,4,6-trimethylphenyl)-amine; 4-[2-Methyl-4-(2,4,6-trimethylphenylamino)-pyrimidine-5-sulfonyl]-benzonitrile; [2-Methyl-5-(toluene-4-sulfonyl)-pyrimidin-4-yl]-(2,4,6-trimethylphenyl)-amine; [2-Methyl-5-(4-pyrimidin-5-yl-benzenesulfonyl)-pyrimidin-4-yl]-(2,4,6-trimethylphenyl)-amine; [2-Methyl-5-(4-pyrimidin-2-yl-benzenesulfonyl)-pyrimidin-4-yl]-(2,4,6-trimethylphenyl)-amine; [2-Methyl-5-(4-pyridin-4-yl-benzenesulfonyl)-pyrimidin-4-yl]-(2,4,6-trimethylphenyl)-amine; [2-Methyl-5-(4-pyridin-2-yl-benzenesulfonyl)-pyrimidin-4-yl]-(2,4,6-trimethylphenyl)-amine; [2-Methyl-5-(4-pyridin-3-yl-benzenesulfonyl)-pyrimidin-4-yl]-(2,4,6-trimethylphenyl)-amine; {5-[4-(4,5-Dihydro-1H-imidazol-2-yl)-benzenesulfonyl]-2-methyl-pyrimidin-4-yl}-(2,4,6-trimethylphenyl)-amine; and {5-[4-(1H-Imidazol-2-yl)-benzenesulfonyl]-2-methyl-pyrimidin-4-yl}-(2,4,6-trimethylphenyl)-amine.

According to a second aspect of the present invention are provided pharmaceutical compositions comprising compounds of the present invention.

According to various embodiments of a third aspect of the present invention are provided methods of treating depression, anxiety, affective disorders, post-traumatic stress disorder, post-operative stress, headache, drug addiction, eating disorders and obesity, sudden death due to cardiac disorders, iritable bowel syndrome, hypertension, syndrome X, inflammatory disorders, stress-induced immune suppression, infertility, stress-induced insomnia and other sleep disorders, seizures, epilepsy, stroke and cerebral ischemia, traumatic brain injury, yet other disorders requiring neuroprotection, drug or alcohol withdrawal symptoms, other disorders including tachycardia, congestive heart failure, osteoporosis, premature birth, psychosocial dwarfism, ulcers, diarrhea, post-operative ileus and yet other conditions the treatment of which can be effected by the antagonism of the CRF-1 receptor by the administration of pharmaceutical compositions comprising compounds of the present invention as described herein.

Other embodiments of the present invention may comprise a suitable combination of two or more of the embodiments and/or aspects disclosed herein.

Yet other embodiments and aspects of the invention will be apparent according to the description provided below.

DETAILED DESCRIPTION OF THE INVENTION

Synthesis

Compounds of the present invention may be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited hereinbelow are hereby incorporated in their entirety herein by reference.

The novel compounds of this invention may be prepared using the reactions and techniques in this section. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Synthesis of various arylsulfonyl pyrimidines is outlined below.

Compounds of formula 7 can be prepared by the method outlined in Scheme 1. An appropriately substituted thiophenol (2) is treated with an ester derivative of acetic acid in the presence or absence of a base in an inert solvent at temperatures ranging from −20° C. to 110° C. wherein a leaving group, such as chloride, bromide, iodide, mesylate, or tosylate is present on the α-carbon of the ester derivative of acetic acid to generate adducts of formula 3. If a base is present, the reaction is carried out in the presence of a base, such as, but not limited to, NaOMe, NaOEt, alkali metal bis(trialkylsilyl)amides (preferably sodium bis(trimethylsilyl)amide), alkaline earth metal hydrides (preferably sodium hydride), alkali metal dialkylamides (preferably lithium di-isopropylamide), alkyl-lithiums carbonates or trialkylamines. Inert solvents include, but are not limited to, tetrahydrofuran, diethyl ether, toluene, dioxane, alcohols, DMF and DMSO (preferably tetrahydrofuran). Treatment of compounds of formula 3 with an appropriate oxidizing agent, such as, but not limited to, a peroxide (preferably meta-chloroperoxybenzoic acid (mCPBA)), oxone, NaIO$_4$ or KMnO$_4$ in an inert organic solvent, preferably methylene chloride, affords the corresponding sulfone. The sulfone can be treated with a lower alkyl orthoformate (R$^a$=C$_1$–C$_4$) in the presence of a lower alkyl anhydride (R$^b$=C$_1$–C$_3$) at temperatures ranging from 25° C. to 140° C. (preferably using conditions described by Neplyuev, et al., *J. Org. Chem. USSR*, 1980, 16, 1275; Patent: SW 433342) to furnish adducts of formula 5 as a mixture of cis- and trans-enol ethers. Cyclization of enol ethers 5 with lower alkyl amidines (C$_{1-6}$) using conditions described by Peters, E., et al. (*J. Org. Chem.*, 1960, 25, 2137) provides pyrimidines 6 wherein R$_1$=alkyl. Adducts wherein R$_1$=NR$^a$R$^c$ or OR$^a$ (R$^a$=C$_{1-4}$, R$^c$=C$_{1-4}$) can be prepared by cyclization of enol ethers 5 with the corresponding N,N-dialkylguanidines or O-alkylisoureas respectively in the presence of a base such as a alkali metal alkoxides (C$_1$–C$_6$), preferably NaOEt, in an organic solvent, such as, but not limited to C$_1$–C$_6$ alcohols (preferably ethanol), dioxane or dimethoxyethane at temperatures ranging from −10° C. to 80° C. Compounds of formula 7 can be formed by treatment of compounds of formula 6 with a chlorinating reagent, preferably phosphorousoxychloride, in the presence or absence of solvent at temperatures ranging from 22° C. to 120° C. Alternatively, compounds related to formula 7 may be formed from 6 upon treatment of 6 with reagents such as, but not limited to, a brominating reagent (preferably phosphorousoxybromide), methanesulfonyl chloride or p-toluenesulfonyl chloride to form the corresponding adduct.

Scheme 1

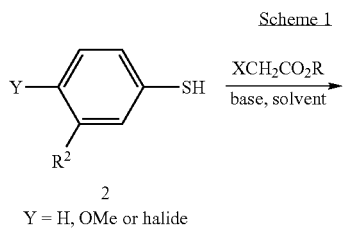

2

Y = H, OMe or halide

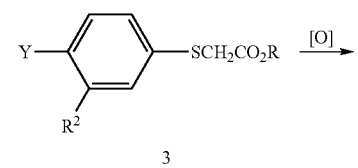

3

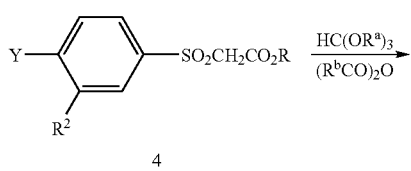

4

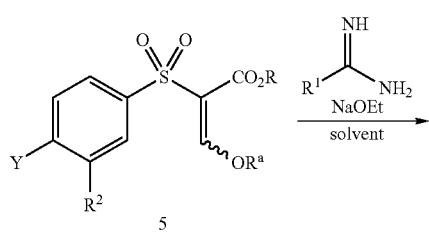

5

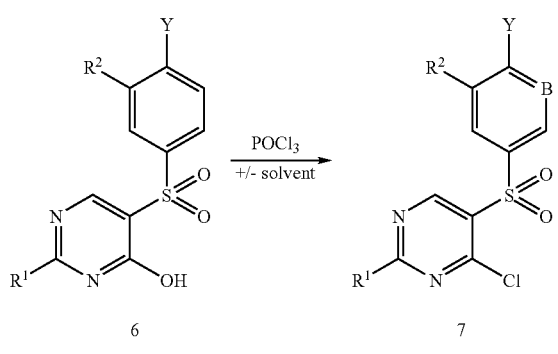

B = CH

Compounds of formula 1 can be prepared from adducts 7 by the methods outlined in Scheme 2. Deprotection of the methoxy group can be effected upon treatment of 7 with $BBr_3$, HBr, LiI in collidine, or related reagents known to those skilled in the art of organic chemistry as described in *Protective Groups in Organic Synthesis* (Greene, Wuts; 3rd ed., 1999, John Wiley & Sons, Inc.). When HBr is used, adducts 8 are formed. An intermediate leading to compounds of formula 1 wherein $R_3$ is joined to the aryl group with an oxygen atom can be prepared by subjecting compounds 8 to alkylation conditions. The reaction is carried out in the presence of an alkylating agent such as an alkyl halide, alkyl mesylate, alkyl tosylate or alkyl triflate in the presence of a base such as $K_2CO_3$, $Na_2CO_3$, $Et_3N$, $i-Pr_2NEt$ or alkali metal alkoxides (preferably KOt-Bu) in a polar organic solvent such as acetone, acetonitrile, dimethoxyethane, dioxane, chloroform or methylene chloride (preferably acetonitrile). Optionally, the reaction can be promoted by the addition of a salt such as KI to form compounds 9. Alternatively, this alkylation reaction can be effected using conditions described by Mitsunobu (Mitsunobu, O., *Synthesis*, 1981, 1). Compounds of formula 1 where B=CH and D=NH can be formed from adducts 9 using conditions described by Wagaw and Buchwald (*J. Org. Chem.*, 1996, 61, 7240–7241).

Alternatively, compounds of formula 1 where B=CH and D=NH can be prepared from adducts 7 in three steps by treatment of 7 with an aniline in the presence or absence of either a transition metal catalyst (such as copper iodide), acid or base and in the presence or absence of solvent at temperatures ranging from 22° C. to 210° C. to form 10. If the reaction is carried out in the presence of a base, bases such as $Et_3N$, $i-Pr_2NEt$, $K_2CO_3$ or $Na_2CO_3$ are used. If the reaction is carried out in the presence of acid, acids such as organic acids are used (preferably p-TsOH). Solvents such as ethylene glycol can be used for this reaction. Deprotection of the methoxy group can be effected upon treatment of 10 with $BBr_3$, HBr, LiI in collidine (preferably LiI in collidine) or related reagents known to those skilled in the art of organic chemistry as described in *Protective Groups in Organic Synthesis*, (Greene, Wuts; 3rd ed., 1999, John Wiley & Sons, Inc.). Intermediates 11 can be alkylated or acetylated to form compounds of formula 1. For alkylation adducts, the reaction is carried out in the presence of an alkylating agent such as an alkyl halide, alkyl mesylate, alkyl tosylate or alkyl triflate in the presence of a base such as $K_2CO_3$, $Na_2CO_3$, $Et_3N$, $i-Pr_2NEt$ or alkali metal alkoxides (preferably $K_2CO_3$) in a polar organic solvent such as acetone, acetonitrile, dimethoxyethane, dioxane, chloroform or methylene chloride (preferably acetonitrile). Optionally, the reaction can be promoted by the addition of a salt such as KI or NaI to form compounds 1. Alternatively, this alkylation reaction can be effected using conditions described by Mitsunobu (Mitsunobu, O., *Synthesis*, 1981, 1). For acylation adducts, compounds 11 are subjected to acylating reagents, such as symmetrical anhydrides, mixed anhydrides, acid halides or esters in the presence of a base, such as, but not limited to, $Et_3N$ or $i-Pr_2NEt$ in the presence or absence of solvent. Alternatively, a carboxylic acid may be coupled with 11 to form an adduct of formula 1 where $R_3$ is an ester using coupling reagents such as, but not limited to, EDC, DCC, BOP, PyBOP and pentafluorophenol in the presence of an organic solvent such as methylene chloride or DMF.

Scheme 2

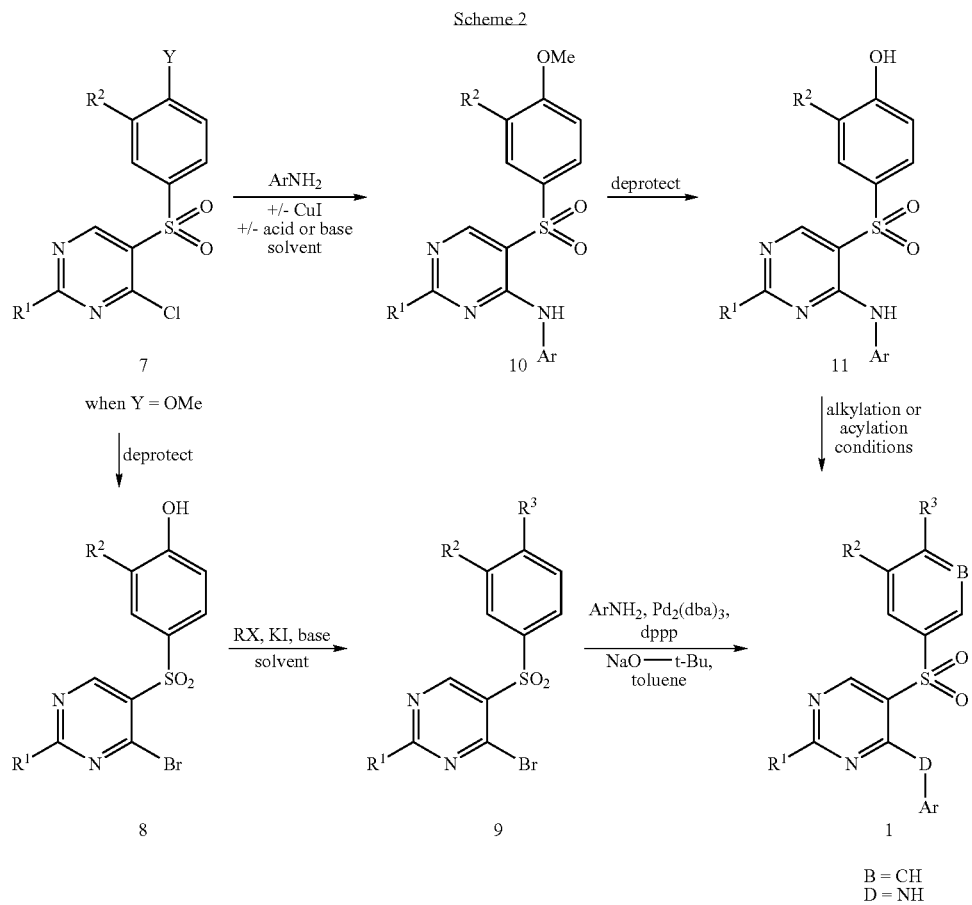

In the case where Y=CHO (10a) the formyl group was converted to the corresponding arylketone 1 by addition of organometallic reagents followed by oxidation of the resulting alcohol (Scheme 3). In the case where Y=Br, 10b (R=Br) could be coupled with various boronic acids in the presence of barium hydroxide and a palladium catalyst to give the corresponding biaryl adducts of formula 1.

Scheme 3

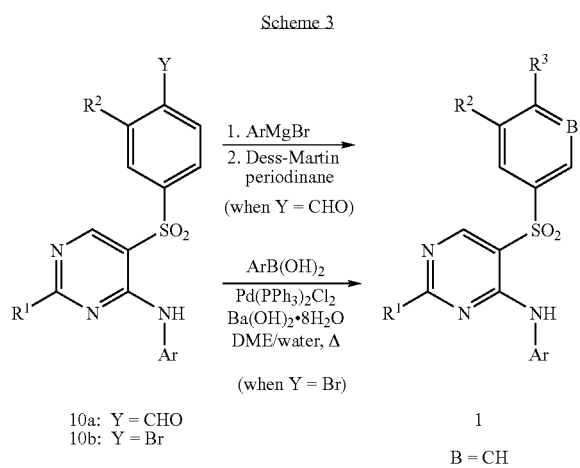

Compounds of formula 1 where B=CH and D=CH$_2$ can be prepared as shown in Scheme 4. Compounds of formula 7 where B=CH and Y=F or OMe are hydrogenated using conditions known to one skilled in the art of organic synthesis. Compounds 7 are placed under a hydrogen atmosphere at pressures ranging from atmospheric pressure to 50 psi in the presence of a metal catalyst such as palladium on carbon (preferably 10% palladium on carbon) in a polar organic solvent such as, but not limited to, lower alkyl alcohols (C$_1$–C$_6$) (preferably ethanol or methanol). The resulting adducts 12 are treated with a benzylic Grignard reagent. The reaction is carried out in either THF or a dialkyl ether (preferably diethyl ether) or a combination thereof at temperatures ranging from −78° C. to 35° C. The Grignard reagent may be commercially available or may need to be prepared. If the Grignard reagent needs to be prepared, it can be prepared from the corresponding benzylic halide (preferably chloride or bromide) by stirring the substrate in diethyl ether in the presence of fresh magnesium turnings using standard literature procedures. Compounds of formula 13 are oxidized using an oxidizing agent such as, but not limited to, TPAP/NMO in a solvent such as methylene chloride to form adducts 14.

If Y=OMe, adducts 14 can be converted to adducts 1, where B=CH$_2$ and D=CH$_2$ using a two step procedure whereby deprotection of the methoxy group can be effected upon treatment of 14 with BBr$_3$, HBr, LiI in collidine (preferably LiI in collidine) or related reagents known to those skilled in the art of organic chemistry as described in *Protective Groups in Organic Synthesis* (Greene, Wuts; 3rd ed., 1999, John Wiley & Sons, Inc.). The resulting intermediates can be alkylated or acetylated to form compounds of formula 1 wherein $R_3$ is joined to the aryl group with an oxygen atom. For alkylation adducts, the reaction is carried out in the presence of an alkylating agent such as an alkyl halide, alkyl mesylate, alkyl tosylate or alkyl triflate in the presence of a base such as $K_2CO_3$, $Na_2CO_3$, $Et_3N$, i-$Pr_2NEt$ or alkali metal alkoxides (preferably $K_2CO_3$) in a polar organic solvent such as acetone, acetonitrile, dimethoxyethane, dioxane, chloroform or methylene chloride (preferably acetonitrile). Optionally, the reaction can be promoted by the addition of a salt such as KI to form compounds 1. Alternatively, this alkylation reaction can be effected using conditions described by Mitsunobu (Mitsunobu, O., *Synthesis*, 1981, 1). For acylation adducts, 1 can be formed by subjection to acylating reagents, such as symmetrical anhydrides, mixed anhydrides, acid halides or esters in the presence of a base, such as, but not limited to, $Et_3N$ or i-$Pr_2NEt$ in the presence or absence of solvent. Alternatively, a carboxylic acid may be coupled with the intermediate phenol to form an adduct of formula 1 where $R_3$ is an ester using coupling reagents such as, but not limited to, EDC, DCC, BOP, PyBOP and pentafluorophenol in the presence of an organic solvent such as methylene chloride or DMF. If Y=F, 14 can be reacted to form 1 using the conditions illustrated in Scheme 5.

Scheme 4

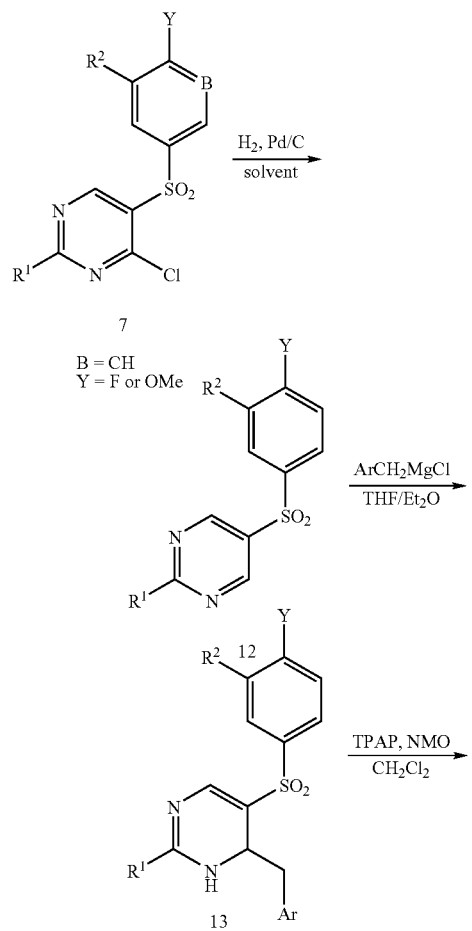

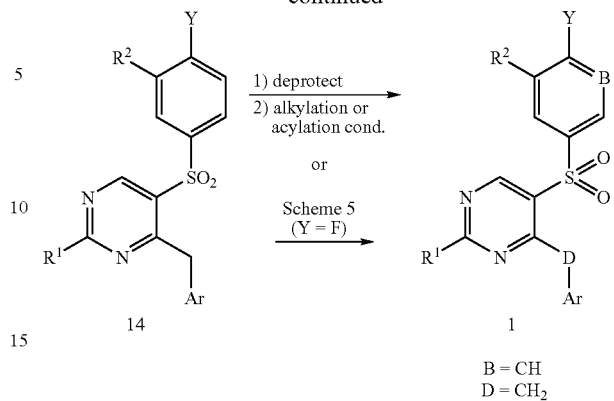

Compounds where $R_3$ is linked to the phenyl group with a nitrogen atom can be prepared from compounds 14 where Y=F (Scheme 5). Compounds 14 can be prepared using the appropriate reactions disclosed in Schemes 1–2. Treatment of 14 with mono or dialkylamines or arylamines (NHR$^d$R$^e$) in the presence or absence of base and in the presence or absence of solvent furnishes adducts 1 where B=CH. The alkyl groups Rd and Re may or may not be joined together to form a ring and may or may not contain heteroatoms. If a base is present, bases such as, but not limited to, $Et_3N$, i-$Pr_2NEt$ alkali earth metal hydrides (preferably sodium hydride), bis(trialkylsilyl)amides (preferably sodium bis(trialkylsilyl)amide), lithium dialkylamides (preferably lithium diisopropyl amide) or alkyl-lithiums can be used. If the reaction is carried out in the presence of a solvent, solvents such as THF, dimethoxyethane, dioxane or DMF are used (preferably dioxane). The reaction is carried out at temperatures ranging from 22° C. to 150° C. If the temperature of the reaction mixture exceeds the boiling point of the solvent, the reaction must be carried out in a pressure vessel.

Scheme 5

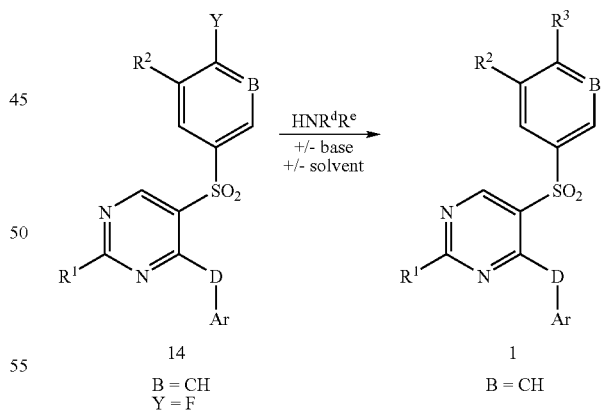

Phenols of formula 11, which can be prepared by the route outlined in Scheme 2, are treated with trifluoromethanesulfonyl chloride in the presence of bases such as $Et_3N$, i-$Pr_2NEt$, collidine or 2,6-dimethylpyridine in a nonprotic organic solvent (preferably dichloromethane) to generate the corresponding triflates 15 (Scheme 6). Compounds of formula 1 can be prepared from 15, wherein $R_3$ is linked to the phenyl group with a carbon atom, by reaction of 15 with an alkyl metal species (metals may include, but are not limited to, boron, tin, zinc, magnesium, and silicon) in the presence or absence of a metal catalyst (preferably PdL$_{2-4}$ where L is a ligand such as, but not limited to, PPh$_3$, Cl, OAc, or dba or a combination thereof) in an aprotic organic solvent such as, but not limited to, CH$_2$Cl$_2$, CHCl$_3$, DME, DMF, toluene or dioxane at temperatures ranging from 22° C. to 180° C. In addition, the reaction may also be carried out in the presence of a base, such as, but not limited to, Na$_2$CO$_3$, K$_2$CO$_3$, Et$_3$N or i-Pr$_2$NEt, (preferably Na$_2$CO$_3$ or Et$_3$N) and in the presence or absence of an inorganic salt (preferably LiCl). In addition, it may be necessary to add a phosphine based ligand (PR$^f_3$, R$^f$=C$_1$–C$_6$ alkyl or phenyl) to the reaction mixture. The conditions described above are known to one skilled in the art of organic synthesis as Stille, Suzuki or Negishi couplings.

such as TPAP/NMO in methylene chloride to furnish an indole of formula 1 (Scheme 7).

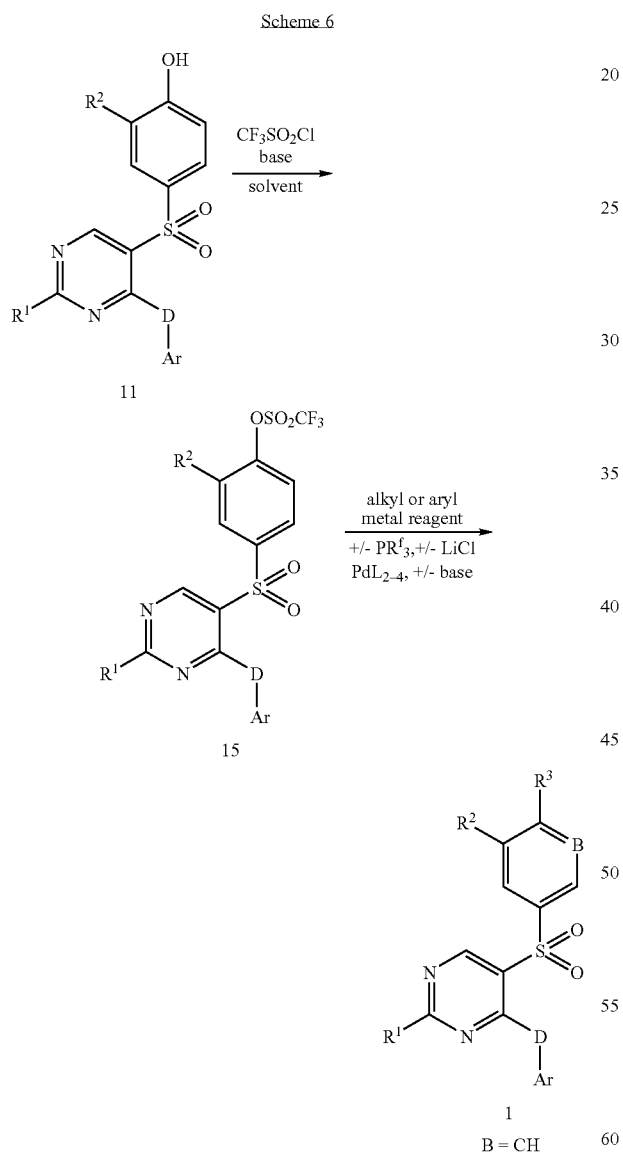

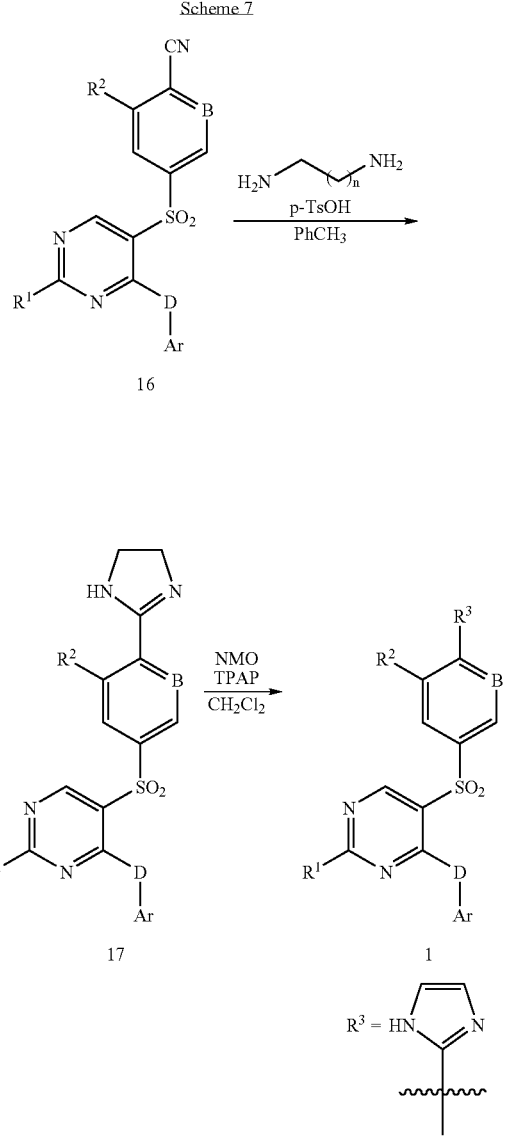

Nitriles 16 are prepared by the method outlined in Scheme 6. Compounds 16 can be further funtionalized by treating with a dialkyl amine where n=1–2. The reaction is carried out in the presence of an acid catalyst (preferably p-TsOH) to form 17. When n=1, 17 is treated with an oxidizing agent Compounds of formula 1 where B=N may be prepared as outlined in Scheme 8. Compounds 18 may be prepared as illustrated in Scheme 1. Treatment of 18 with alcohols R$^d$OH (R$^d$=alkyl or aryl) or mono or dialkylamines or arylamines (NHR$^d$R$^e$) in the presence or absence of base and in the presence or absence of solvent furnishes adducts 19. The alkyl groups R$^d$ and R$^e$ may or may not be joined together to form a ring and may or may not contain heteroatoms. If a base is present, bases such as, but not limited to, Et$_3$N, i-Pr$_2$NEt alkali earth metal hydrides (preferably sodium hydride), bis(trialkylsilyl)amides (preferably sodium bis(trialkylsilyl)amide), lithium dialkylamides (preferably lithium diisopropyl amide) or alkyl-lithiums can be used. If the reaction is carried out in the presence of a solvent, solvents such as THF, dimethoxyethane, dioxane or DMF are used (preferably dioxane). The reaction is carried out at temperatures ranging from 22° C. to 150° C. If the temperature of the reaction mixture exceeds the boiling point of the solvent, the reaction must be carried out in a pressure vessel. Compounds of formula 19 can be prepared from 18, wherein $R_3$ is linked to the phenyl group with a carbon atom, by reaction of 18 with an alkyl metal species (metals may include, but are not limited to, boron, tin, zinc, magnesium, and silicon) in the presence or absence of a metal catalyst (preferably $PdL_{2-4}$ where L is a ligand such as, but not limited to, $PPh_3$, Cl, OAc, or dba or a combination thereof) in an aprotic organic solvent such as, but not limited to, $CH_2Cl_2$, $CHCl_3$, DME, DMF, toluene or dioxane at temperatures ranging from 22° C. to 180° C. In addition, the reaction may also be carried out in the presence of a base, such as, but not limited to, $Na_2CO_3$, $K_2CO_3$, $Et_3N$ or $i-Pr_2NEt$, (preferably $Na_2CO_3$ or $Et_3N$) and in the presence or absence of an inorganic salt (preferably LiCl). In addition, it may be necessary to add a phosphine based ligand ($PR'_3$, $R^f=C_1-C_6$ alkyl or phenyl) to the reaction mixture. The conditions described above are known to one skilled in the art of organic synthesis as Stille (Stille, J. K., *Angew, Chem., Int. Ed. Engl.*, 1986, 25, 508–524), Suzuki (Suzuki, A., *Pure and Appl. Chem.*, 1985, 57, 1749–1758), Negishi (Negishi, E., *Acc. Chem. Res.*, 1982, 15, 240–348) or Kumada (Tamao, K.; Sumitani, K.; Kiso, Y.; Zembayashi, M.; Fujioka, A.; Kodma, S.-i.; Nakajima, I.; Minato, A.; Kumada, M., *Bull. Chem. Soc. Jpn.*, 1976, 49, 1958–1969) couplings. Alternatively, in place of a coupling reaction, a carbon nucleophile, such as NaCN, may be reacted with 18 to form compounds of formula 19.

Compounds for formula 1 where B=N and D=NH may be formed from adducts 19 by treatment of 19 with an aniline in the presence or absence of either acid or base and in the presence or absence of solvent at temperatures ranging from 22° C. to 210° C. If the reaction is carried out in the presence of a base, bases such as $Et_3N$, $i-Pr_2NEt$, $K_2CO_3$ or $Na_2CO_3$ are used. If the reaction is carried out in the presence of acid, acids such as organic acids are used (preferably p-TsOH). If the reaction is carried out in the presence of a solvent, an organic solvent such as an alcohol or ethylene glycol is used. Compounds for formula 1 where B=N and $D=CH_2$ may be formed from adducts 19 by employing the reactions described in steps 1–3 of Scheme 4.

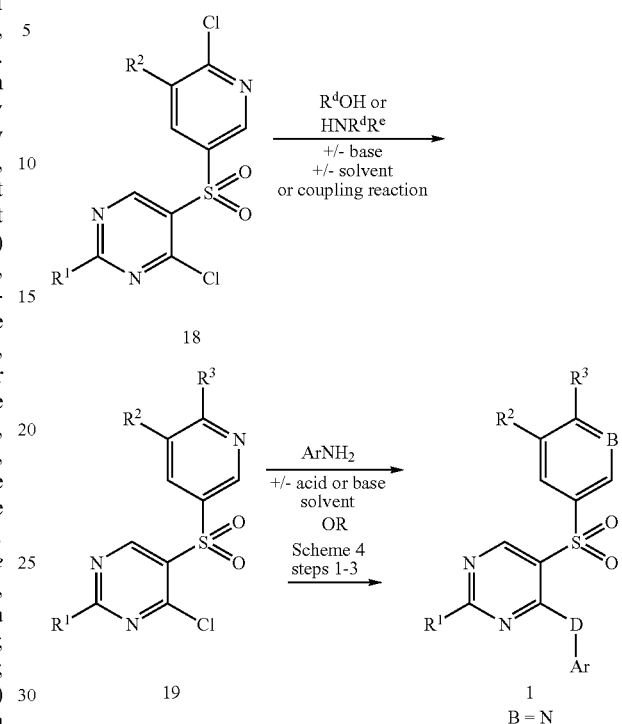

Compounds of formula 1 where $R_2$ is a substituent other than H or $R_2$ and $R_3$ are both substituents other than H can be prepared using the routes in Schemes 1–8 by starting with the appropriate starting materials.

Various analogs that may be synthesized using Schemes 1–7 are listed in Table 1. Compounds having a designation of a, b, c or d were tested in the CRF assays described below and exhibited the following levels of activity: a, $K_i \leq 100$ nM; b, $100\ nM<K_i\leq 500$ nM, c, $500\ nM<K_i\leq 5,000$ nM, d—activity reported in percent inhibition at 10 μM. Compounds not having such a designation are prophetic examples.

TABLE 1

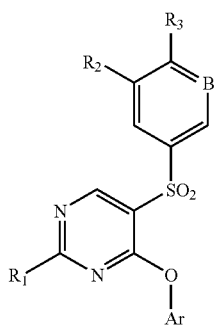

| Ex | B | D | $R_1$ | $R_2$ | $R_3$ | Ar | Mp (° C.) | activity |
|---|---|---|---|---|---|---|---|---|
| 1 | CH | NH | Me | H | OMe | 2,4,6-Me$_3$—Ph | 153–155 | b |
| 2 | CH | NH | Me | H | OH | 2,4,6-Me$_3$—Ph | 246–248 | c |

TABLE 1-continued

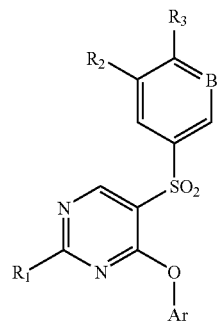

| Ex | B | D | R₁ | R₂ | R₃ | Ar | Mp (° C.) | activity |
|----|----|----|----|----|----|----|----|----|
| 3 | CH | NH | Me | H | OAc | 2,4,6-Me₃—Ph | 142–144 | c |
| 4 | CH | NH | Me | H | OBn | 2,4,6-Me₃—Ph | 166–168 | a |
| 5 | CH | NH | Me | H | OBn | 2-Me-4-OMe—Ph | 110–114 | b |
| 6 | CH | NH | Me | H | OBn | 2-Me-4-OMe-3-pyridyl | 160–165 | d |
| 7 | CH | NH | Me | OBn | H | 2,4,6-Me₃—Ph | 112–115 | b |
| 8 | CH | NH | OMe | OBn | H | 2,4,6-Me₃—Ph | oil | d |
| 9 | CH | NH | NMe₂ | OBn | H | 2,4,6-Me₃—Ph | 52–58 | c |
| 10 | CH | NH | Me | H | 2-OMe—OBn | 2,4,6-Me₃—Ph | 200–202 | a |
| 11 | CH | NH | Me | H | 3,5-OMe₂—OBn | 2,4,6-Me₃—Ph | oil | a |
| 12 | CH | NH | Me | H | OBn | 2,4-OMe₂—Ph | solid | d |
| 13 | CH | CH₂ | Me | H | OMe | 2,4,6-Me₃—Ph | 150–152 | b |
| 14 | CH | CH₂ | Me | H | OBn | 2,4,6-Me₃—Ph | 166–168 | a |
| 15 | CH | NH | Me | H | F | 2,4,6-Me₃—Ph | 191–193 | b |
| 16 | CH | NH | Me | H | morpholin-4-yl | 2,4,6-Me₃—Ph | 221–223 | d |
| 17 | CH | NH | Me | H | 4-Me-piperazin-1-yl | 2,4,6-Me₃—Ph | oil | d |
| 18 | CH | NH | Me | H | imidazol-1-yl | 2,4,6-Me₃—Ph | 230–232 | d |
| 19 | CH | NH | Me | H | pyrrolidin-1-yl | 2,4,6-Me₃—Ph | 196–198 | d |
| 20 | CH | NH | Me | H | NHBn | 2,4,6-Me₃—Ph | 200–202 | b |
| 21 | CH | NH | Me | H | N(Me)Bn | 2,4,6-Me₃—Ph | 146–148 | a |
| 22 | CH | NH | Me | H | CN | 2,4,6-Me₃—Ph | 258–260 | c |
| 23 | CH | NH | Me | H | Me | 2,4,6-Me₃—Ph | 202–204 | b |
| 24 | CH | NH | Me | H | pyrimidin-5-yl | 2,4,6-Me₃—Ph | 210–212 | d |
| 25 | CH | NH | Me | H | pyrimidin-2-yl | 2,4,6-Me₃—Ph | 215–217 | a |
| 26 | CH | NH | Me | H | pyridin-4-yl | 2,4,6-Me₃—Ph | 232–234 | c |
| 27 | CH | NH | Me | H | pyridin-2-yl | 2,4,6-Me₃—Ph | 201–203 | a |
| 28 | CH | NH | Me | H | pyridin-3-yl | 2,4,6-Me₃—Ph | 190–192 | c |
| 29 | CH | NH | Me | H | 4,5-dihydro-1H-imidazol-2-yl | 2,4,6-Me₃—Ph | 240–242 | d |
| 30 | CH | NH | Me | H | 1H-imidazol-2-yl | 2,4,6-Me₃—Ph | 282–284 | d |
| 31 | CH | CH₂ | Me | H | 2-OMe—OBn | 2-Me-4-OMe—Ph | | |
| 32 | CH | CH₂ | Me | H | 2-OMe—OBn | 2-Cl-4-OMe-5-F—Ph | | |
| 33 | CH | CH₂ | Me | H | 2-OMe—OBn | 2-Cl-4-NMe₂-5-F—Ph | | |
| 34 | CH | CH₂ | Me | H | 2-OMe—OBn | 2-Me-4,5-OMe₂—Ph | | |
| 35 | CH | CH₂ | Me | H | 2-OMe—OBn | 2-Cl-4-OCHF₂—Ph | | |
| 36 | CH | CH₂ | Me | H | 2-OMe—OBn | 2-Cl-4,5-OMe₂—Ph | | |
| 37 | CH | CH₂ | Me | H | 2-OMe—OBn | 2-Cl-4-SO₂Me—Ph | | |
| 38 | CH | CH₂ | Me | H | 2-OMe—OBn | 2-CN-4-Cl—Ph | | |
| 39 | CH | CH₂ | Me | H | Et | 2-Cl-4-OMe—Ph | | |
| 40 | CH | CH₂ | Me | H | OH | 2,4,6-Me₃—Ph | | |
| 41 | CH | CH₂ | Me | H | Et | 2,4,5-Me₃—Ph | | |
| 42 | CH | CH₂ | Me | H | OEt | 2,4,6-Me₃—Ph | | |
| 43 | CH | CH₂ | Me | H | Oallyl | 2,4,6-Me₃—Ph | | |
| 44 | CH | CH₂ | Me | H | OC₃H₆CN | 2,4,6-Me₃—Ph | | |
| 45 | CH | CH₂ | Me | H | OC₄H₈CN | 2,4,6-Me₃—Ph | | |
| 46 | CH | CH₂ | Me | H | OC₃H₆OH | 2,4,6-Me₃—Ph | | |
| 47 | CH | CH₂ | Me | H | OCH₂CO₂Et | 2,4,6-Me₃—Ph | | |
| 48 | CH | CH₂ | Me | H | OEtCHCO₂Et | 2,4,6-Me₃—Ph | | |
| 49 | CH | CH₂ | Me | H | OCH₂(2-pyridyl) | 2,4,6-Me₃—Ph | | |
| 50 | CH | CH₂ | Me | H | OCH₂(3,5-Cl₂-4-pyridyl) | 2,4,6-Me₃—Ph | | |
| 51 | CH | CH₂ | Me | H | OCH₂(2-Me-4-thiazolyl) | 2,4,6-Me₃—Ph | | |
| 52 | CH | CH₂ | Me | H | 4-F—OBn | 2,4,6-Me₃—Ph | | |
| 53 | CH | CH₂ | Me | H | 4-CN—OBn | 2,4,6-Me₃—Ph | | |
| 54 | CH | CH₂ | Me | H | 3-CN—OBn | 2,4,6-Me₃—Ph | | |
| 55 | CH | CH₂ | Me | H | 3-CO₂Me—OBn | 2,4,6-Me₃—Ph | | |
| 56 | CH | CH₂ | Me | H | 3-OMe—OBn | 2,4,6-Me₃—Ph | | |
| 57 | CH | CH₂ | Me | H | 2-OMe—OBn | 2,4,6-Me₃—Ph | | |
| 58 | CH | CH₂ | Me | H | 2-CN—OBn | 2,4,6-Me₃—Ph | | |
| 59 | CH | CH₂ | Me | H | 2-NO₂—OBn | 2,4,6-Me₃—Ph | | |
| 60 | CH | CH₂ | Me | H | 3,5-OMe₂—OBn | 2,4,6-Me₃—Ph | | |
| 61 | CH | CH₂ | Me | H | 2,5-OMe₂—OBn | 2,4,6-Me₃—Ph | | |
| 62 | CH | CH₂ | Me | H | 2,3-OMe₂—OBn | 2,4,6-Me₃—Ph | | |

TABLE 1-continued

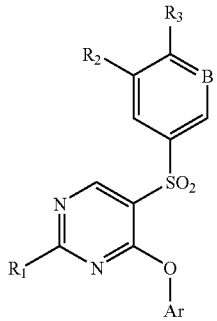

| Ex | B | D | $R_1$ | $R_2$ | $R_3$ | Ar | Mp (° C.) | activity |
|---|---|---|---|---|---|---|---|---|
| 63 | CH | $CH_2$ | Me | H | 2,3-$F_2$—OBn | 2,4,6-$Me_3$—Ph | | |
| 64 | CH | $CH_2$ | Me | H | 2-F-6-$NO_2$—OBn | 2,4,6-$Me_3$—Ph | | |
| 65 | CH | $CH_2$ | Me | H | 3-Ac-6-OMe—OBn | 2,4,6-$Me_3$—Ph | | |
| 66 | CH | $CH_2$ | Me | H | 2,6-$Me_2$—OBn | 2,4,6-$Me_3$—Ph | | |
| 67 | CH | $CH_2$ | Me | Cl | F | 2,4,6-$Me_3$—Ph | | |
| 68 | CH | $CH_2$ | Me | Me | Me | 2,4,6-$Me_3$—Ph | | |
| 69 | CH | $CH_2$ | Me | OMe | OMe | 2,4,6-$Me_3$—Ph | | |
| 70 | CH | $CH_2$ | Me | Cl | Cl | 2,4,6-$Me_3$—Ph | | |
| 71 | CH | $CH_2$ | Me | H | Me | 2,4,6-$Me_3$—Ph | | |
| 72 | CH | $CH_2$ | Me | H | Et | 2,4,6-$Me_3$—Ph | | |
| 73 | CH | $CH_2$ | Me | H | isopropyl | 2,4,6-$Me_3$—Ph | | |
| 74 | CH | $CH_2$ | Me | H | $OCF_3$ | 2,4,6-$Me_3$—Ph | | |
| 75 | CH | $CH_2$ | Me | H | F | 2,4,6-$Me_3$—Ph | | |
| 76 | CH | $CH_2$ | Me | H | Br | 2,4,6-$Me_3$—Ph | | |
| 77 | CH | $CH_2$ | Me | H | ethyne | 2,4,6-$Me_3$—Ph | | |
| 78 | CH | $CH_2$ | Me | H | Ph | 2,4,6-$Me_3$—Ph | | |
| 79 | CH | $CH_2$ | Me | H | 2-OMePh | 2,4,6-$Me_3$—Ph | | |
| 80 | CH | $CH_2$ | Me | H | $CH_2$N-mesityl | 2,4,6-$Me_3$—Ph | | |
| 81 | CH | $CH_2$ | Me | H | $CH_2OH$ | 2,4,6-$Me_3$—Ph | | |
| 82 | CH | $CH_2$ | Me | H | CHO | 2,4,6-$Me_3$—Ph | | |
| 83 | CH | $CH_2$ | Me | H | CH(OH)Ph | 2,4,6-$Me_3$—Ph | | |
| 84 | CH | $CH_2$ | Me | H | COPh | 2,4,6-$Me_3$—Ph | | |
| 85 | CH | $CH_2$ | Me | H | $CH_2OAc$ | 2,4,6-$Me_3$—Ph | | |
| 86 | CH | $CH_2$ | Me | OMe | H | 2,4,6-$Me_3$—Ph | | |
| 87 | CH | $CH_2$ | Me | OH | H | 2,4,6-$Me_3$—Ph | | |
| 88 | CH | $CH_2$ | Me | OEt | H | 2,4,6-$Me_3$—Ph | | |
| 89 | CH | $CH_2$ | Me | Oallyl | H | 2,4,6-$Me_3$—Ph | | |
| 90 | CH | $CH_2$ | Me | OBn | H | 2,4,6-$Me_3$—Ph | | |
| 91 | CH | $CH_2$ | Me | 4-F—OBn | H | 2,4,6-$Me_3$—Ph | | |
| 92 | CH | $CH_2$ | Me | 3-OMe—OBn | H | 2,4,6-$Me_3$—Ph | | |
| 93 | CH | $CH_2$ | Me | 3,5-$OMe_2$—OBn | H | 2,4,6-$Me_3$—Ph | | |
| 94 | CH | $CH_2$ | Me | $OCH_2$(4-Cl-3-pyridyl) | H | 2,4,6-$Me_3$—Ph | | |
| 95 | CH | $CH_2$ | Me | $OCH_2$(3,5-$Cl_2$-4-pyridyl) | H | 2,4,6-$Me_3$—Ph | | |
| 96 | CH | $CH_2$ | Me | H | Et | 2,4-$Me_2$—Ph | | |
| 97 | CH | $CH_2$ | Me | H | Et | 2-Me-4-OMe—Ph | | |
| 98 | CH | $CH_2$ | Me | H | Et | 2,4-$(OMe)_2$—Ph | | |
| 99 | CH | NH | CN | H | 2-OMe—OBn | 2,4,6-$Me_3$—Ph | | |
| 100 | CH | NH | CN | H | 2-OMe—OBn | 2,4-$Me_2$—Ph | | |
| 101 | CH | NH | CN | H | 2-OMe—OBn | 2-Me-4-OMe—Ph | | |
| 102 | CH | NH | CN | H | 2-OMe—OBn | 2,4-$(OMe)_2$—Ph | | |
| 103 | CH | NH | Me | H | 2-OMe—OBn | 2,6-$Cl_2$-4-$OCF_3$—Ph | | |
| 104 | CH | NH | Me | H | 2-OMe—OBn | 2,6-$Cl_2$-4-$CF_3$—Ph | | |
| 105 | CH | NH | Me | H | 2-OMe—OBn | 2,6-$Cl_2$-4-CN—Ph | | |
| 106 | CH | NH | Me | H | 2-OMe—OBn | 2-Cl-4-CN-6-Me—Ph | | |
| 107 | CH | NH | Me | H | 2-OMe—OBn | 2,6-$Cl_2$-4-OMe—Ph | | |
| 108 | CH | NH | Me | H | 2-OMe—OBn | 2,6-$Cl_2$—$OCHF_2$—Ph | | |
| 109 | CH | NH | Me | H | 2-OMe—OBn | 2-Cl-4-$OCF_3$-6-Me—Ph | | |
| 110 | CH | NH | Me | H | 2-OMe—OBn | 2,4-$OMe_2$-3-pyridyl | | |
| 111 | CH | NH | Me | H | 2-OMe—OBn | 2,4-Me-3-pyridyl | | |
| 112 | CH | NH | Me | H | 2-OMe—OBn | 2-Me-4-oMe-3-pyridyl | | |
| 113 | CH | NH | Me | H | 2-OMe—OBn | 2,6-$Me_2$-4-OMe-3-pyridyl | | |
| 114 | CH | NH | Me | H | 2-OMe—OBn | 2-$CF_3$-4-OMe-3-pyridyl | | |
| 115 | CH | NH | Me | H | 2-OMe—OBn | 2-OMe-4-$CF_3$-3-pyridyl | | |
| 116 | CH | NH | Me | H | 2-OMe—OBn | 2-Me-4-$CF_3$-3-pyridyl | | |
| 117 | N | NH | Me | H | 2-OMe—OBn | 2,4,6-$Me_3$—Ph | | |
| 118 | N | NH | Me | H | 3-OMe—OBn | 2,4,6-$Me_3$—Ph | | |
| 119 | N | NH | Me | H | 4-OMe—OBn | 2,4,6-$Me_3$—Ph | | |
| 120 | N | NH | Me | H | OMe | 2,4,6-$Me_3$—Ph | | |
| 121 | N | NH | Me | H | OBn | 2,4,6-$Me_3$—Ph | | |

TABLE 1-continued

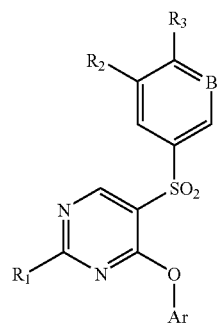

| Ex | B | D | R₁ | R₂ | R₃ | Ar | Mp (° C.) | activity |
|---|---|---|---|---|---|---|---|---|
| 122 | N | NH | Me | H | Oet | 2,4,6-Me₃—Ph | | |
| 123 | N | NH | Me | H | Oallyl | 2,4,6-Me₃—Ph | | |
| 124 | N | NH | Me | H | 2-CN—OBn | 2,4,6-Me₃—Ph | | |
| 125 | N | NH | Me | H | 3-CN—OBn | 2,4,6-Me₃—Ph | | |

Also provided herein are pharmaceutical compositions comprising compounds of this invention and a pharmaceutically acceptable carrier, which are media generally accepted in the art for the delivery of biologically active agents to animals, in particular, mammals. Pharmaceutically acceptable carriers are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences*, 17$^{th}$ ed., Mack Publishing Company, Easton, Pa., 1985, the contents of which are incorporated herein by reference.

This invention thus further provides a method of treating a subject afflicted with a disorder characterized by CRF overexpression, such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

This invention is described in the following examples, which those of ordinary skill in the art will readily understand are not limiting on the invention as defined in the claims which follow thereafter.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, μL for microliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio, "α", "β", "R" and "S" are stereochemical designations familiar to those skilled in the art.

Example 1

[5-(4-Methoxybenzenesulfonyl)-2-methylpyrimidin-4-yl]-(2,4,6-trimethylphenyl)-amine

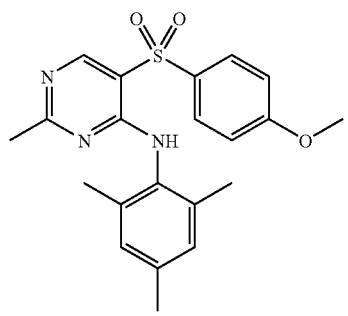

Part A. (4-Methoxy-phenylsulfanyl)-acetic acid ethyl ester

To a suspension of sodium hydride (60% in oil, 1.71 g, 42.8 mmol) in THF (40 mL), 4-methoxybenzenethiol (5.0 g, 35.7 mmol) was added dropwise at room temperature over a period of 10 min. The mixture was stirred at room temperature under $N_2$ for 10 min and then cooled to 0° C. Ethyl bromoacetate (4.0 mL, 36 mmol) was added dropwise at 0° C. over a period of 10 min. The reaction mixture was stirred at room temperature for 30 min and then quenched with saturated ammonium chloride. The organic layer was separated and the aqueous layer was extracted with ethyl acetate (2×). The combined organic layers were washed with brine, dried over $Na_2SO_4$, filtered and concentrated in vacuo. The residue was purified by chromatography on silica gel (1:9 ethyl acetate/hexanes) to provide (4-methoxy-phenylsulfanyl)-acetic acid ethyl ester (7.9 g, 98%) as colorless oil: $^1$H NMR (300 MHz, CDCl$_3$) δ 7.42 (d, J=6.6 Hz, 2H), 6.84 (d, J=6.6 Hz, 2H), 4.11 (q, J=7.1 Hz, 2H), 3.80 (s, 3H), 3.51 (s, 2H), 1.21 (t, J=7.1 Hz, 3H); ESI MS m/z 227 [(M+H)$^+$, calcd for $C_{11}H_{15}O_3S$, 227.0].

Part B. (4-Methoxy-benzenesulfonyl)-acetic acid ethyl ester

To a solution of mCPBA (18.0 g, 105 mmol) in methylene chloride (50 mL), (4-methoxy-phenylsulfanyl)-acetic acid ethyl ester (7.9 g, 35 mmol) in methylene chloride (50 mL) was added dropwise at 0° C. over a period of 20 min. The reaction mixture was stirred at room temperature overnight and then diluted with ethyl acetate (300 mL). The mixture was washed with 1 N NaOH (3×50 mL) and brine (20 mL), dried over $Na_2SO_4$, filtered and concentrated in vacuo. The residue was purified by chromatography on silica gel (1:1 ethyl acetate/hexanes) to provide the corresponding sulfone (8.3 g, 92%) as colorless oil: $^1$H NMR (300 MHz, CDCl$_3$) δ 7.88 (d, J=7.0 Hz, 2H), 7.03 (d, J=7.0 Hz, 2H), 4.16 (q, J=7.1 Hz, 2H), 4.08 (s, 2H), 3.90 (s, 3H), 1.22 (t, J=7.1 Hz, 3H); ESI MS m/z 259 [(M+H)$^+$, calcd for $C_{11}H_{15}O_5S$, 259.0].

Part C. 3-Ethoxy-2-(4-methoxy-benzenesulfonyl)-acrylic acid ethyl ester

A mixture of (4-methoxy-benzenesulfonyl)-acetic acid ethyl ester (8.3 g, 32 mmol) and triethyl orthoformate (16 mL, 96 mmol) in acetic anhydride (20 mL) was refluxed under $N_2$ for 16 h. Solvents were removed by distillation (keep the temperature of oil bath below 180° C.). The residue was purified by chromatography on silica gel (1:1 ethyl acetate/hexanes) to provide the desired product as a mixture of isomers (a mixture of trans- and cis-isomers, 5.3 g, 53%) as a light yellow oil.

Isomer A: $^1$H NMR (300 MHz, CDCl$_3$) δ 8.10 (s, 1H), 7.86 (d, J=7.0 Hz, 2H), 6.96 (d, J=7.0 Hz, 2H), 4.36 (q, J=7.1 Hz, 2H), 4.13 (q, J=7.1 Hz, 2H), 3.86 (s, 3H), 1.45 (t, J=7.1 Hz, 3H); 1.18 (t, J=7.1 Hz, 3H); ESI MS m/z 315 [(M+H)$^+$, calcd for $C_{14}H_{19}O_6S$, 315.1].

Isomer B: $^1$H NMR (300 MHz, CDCl$_3$) δ 7.94 (d, J=7.0 Hz, 2H), 7.76 (s, 1H), 6.96 (d, J=7.0 Hz, 2H), 4.31 (q, J=7.1 Hz, 2H), 4.15 (q, J=7.1 Hz, 2H), 3.86 (s, 3H), 1.43 (t, J=7.1 Hz, 3H), 1.23 (t, J=7.1 Hz, 3H); ESI MS m/z 315 [(M+H)$^+$, calcd for $C_{14}H_{19}O_6S$, 315.1].

Part D. 5-(4-Methoxy-benzenesulfonyl)-2-methyl-pyrimidin-4-ol

To a solution of acetamide hydrochloride (0.76 g, 8.0 mmol) in ethanol (10 mL), sodium ethoxide (2.18 g, 32 mmol) was added at 0° C. The mixture was stirred at 0° C. for 5 min and then 3-ethoxy-2-(4-methoxy-benzenesulfonyl)-acrylic acid ethyl ester (2.51 g, 8.0 mmol) in ethanol (10 mL) was added dropwise at 0° C. over a period of 10 min. The reaction mixture was slowly warmed to room temperature and stirred under $N_2$ overnight. The mixture was diluted with methylene chloride (300 mL), washed with brine, dried over $Na_2SO_4$, filtered and concentrated in vacuo. The residue was purified by recrystallization in acetone to afford 5-(4-methoxy-benzenesulfonyl)-2-methyl-pyrimidin-4-ol (1.57 g, 70%) as a white solid: $^1$H NMR (300 MHz, CDCl$_3$) δ 8.55 (s, 1H), 7.90 (d, J=7.0 Hz, 2H), 7.11 (d, J=7.0 Hz, 2H), 3.83 (s, 3H), 3.33 (s, 1H), 2.34 (s, 3H); ESI MS m/z 281 [(M+H)$^+$, calcd for $C_{12}H_{13}N_2O_4S$, 281.1].

Part E. 4-Chloro-5-(4-methoxy-benzenesulfonyl)-2-methyl-pyrimidine

A mixture of 5-(4-methoxy-benzenesulfonyl)-2-methyl-pyrimidin-4-ol (200 mg, 0.714 mmol) in phosphorus oxychloride (4 mL) was refluxed under $N_2$ for 2 h and then cooled to room temperature. Solvents were removed in vacuo, and the residue was poured into ice water with stirring. The mixture was neutralized with saturated sodium bicarbonate to pH~7 and extracted with methylene chloride (3×). The combined organic layers were washed with brine, dried over $Na_2SO_4$, filtered and concentrated in vacuo. The residue was purified by chromatography on silica gel (1:1 ethyl acetate/hexanes) to provide 4-chloro-5-(4-methoxy-benzenesulfonyl)-2-methyl-pyrimidine (177 mg, 83%) as a light yellow solid: $^1$H NMR (300 MHz, CDCl$_3$) δ 9.32 (s, 1H), 7.93 (d, J=7.2 Hz, 2H), 7.01 (d, J=7.2 Hz, 2H), 3.89 (s, 3H), 2.77 (s, 3H); ESI MS m/z 299 [(M+H)$^+$, calcd for $C_{12}H_{12}ClN_2O_3S$, 299.0].

Part F. [5-(4-Methoxy-benzenesulfonyl)-2-methyl-pyrimidin-4-yl]-(2,4,6-trimethylphenyl)-amine To a solution of 2,4,6-trimethylaniline (0.089 mL, 0.64 mmol) in THF (2 mL), NaHMDS (1.0 M in THF, 0.64 mL, 0.64 mmol) was added dropwise at 0° C. The mixture was stirred under $N_2$ at 0° C. for 10 min, and then 4-chloro-5-(4-methoxy-benzenesulfonyl)-2-methyl-pyrimidine (158 mg, 0.53 mmol) in THF (3 mL) was added dropwise at 0° C. The reaction mixture was stirred at room temperature for 1 h, and then quenched with saturated ammonium chloride. The organic layer was separated and the aqueous layer was extracted with ethyl acetate (2×). The combined organic layers were washed with brine, dried over $Na_2SO_4$, filtered and concentrated in vacuo. The residue was purified by chromatography on silica gel (1:2 ethyl acetate/hexanes) to provide the target compound (95 mg, 45%) as a light yellow solid: mp 153–155° C.; $^1$H NMR (300 MHz, CDCl$_3$) δ 8.74

(s 1H), 8.22 (br s, 1H), 7.88 (d, J=7.0 Hz, 2H), 6.98 (d, J=7.0 Hz, 1H), 6.91 (s, 2H), 3.86 (s, 3H), 2.38 (s, 3H), 2.30 (s, 3H), 2.01 (s, 6H); ESI MS m/z 398 [(M+H)$^+$, calcd for $C_{21}H_{24}N_3O_3S$, 398.2].

Example 2

4-[2-Methyl-4-(2,4,6-trimethylphenylamino)-pyrimidine-5-sulfonyl]-phenol

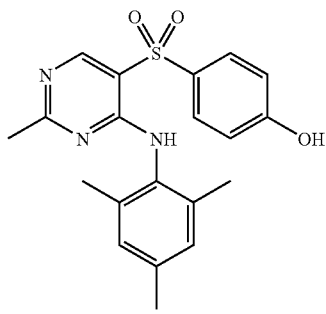

A mixture of [5-(4-methoxy-benzenesulfonyl)-2-methyl-pyrimidin-4-yl]-(2,4,6-trimethylphenyl)-amine (300 mg, 0.75 mmol), prepared as described in Example 1, LiI (2.0 g, 15 mmol) and 2,4,6-collidine (5 mL) was refluxed under N$_2$ for 2 h and then cooled to room temperature. The reaction mixture was diluted with Et$_2$O, and extracted (4×) with 2 N NaOH. The combined aqueous layers were washed with ether, neutralized with 3 N HCl to pH=7.0 and then were extracted three times with CH$_2$Cl$_2$. The combined organic layers were washed with brine, dried over Na$_2$SO$_4$, filtered and concentrated in vacuo. The residue was purified by chromatography on silica gel (50:50 hexanes/EtOAc) to provide the desired product (271 mg, 93%) as a white solid: mp 246–248° C.; $^1$H NMR (300 MHz, CDCl$_3$) δ 8.69 (s, 1H), 8.30 (br s, 1H), 7.82 (d, J=8.7 Hz, 2H), 6.92 (s, 2H), 6.89 (d, J=8.7 Hz, 2H), 2.40 (s, 3H), 2.31 (s, 3H), 2.03 (s, 6H); APCI MS m/z 384 [(M+H)$^+$, calcd for $C_{20}H_{22}N_3O_3S$, 384.1].

Example 3

Acetic acid 4-[2-methyl-4-(2,4,6-trimethylphenylamino)-pyrimidine-5-sulfonyl]-phenyl ester

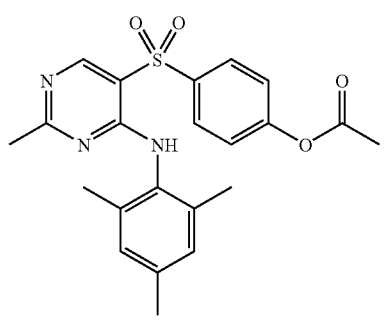

A mixture of 4-[2-methyl-4-(2,4,6-trimethyl-phenylamino)-pyrimidine-5-sulfonyl]-phenol (46 mg, 0.12 mmol), prepared as described in Example 2, acetic anhydride (0.023 mL, 0.24 mmol), triethylamine (0.05 mL, 0.36 mmol) and CH$_2$Cl$_2$ (4 mL) was stirred at room temperature under N$_2$ for 4 h. The reaction mixture was treated with saturated sodium bicarbonate, and extracted (3×) with CH$_2$Cl$_2$. The combined organic layers were washed with brine, dried over Na$_2$SO$_4$, filtered and concentrated in vacuo. The residue was purified by chromatography on silica gel (50:50 hexanes/EtOAc) to provide the target compound (47 mg, 92%) as a white solid: mp 142–144° C.; $^1$H NMR (300 MHz, CDCl$_3$) δ 8.76 (s, 1H), 8.23 (br s, 1H), 7.99 (d, J=8.7 Hz, 2H), 7.29 (d, J=8.7 Hz, 2H), 6.92 (s, 2H), 2.40 (s, 3H), 2.33 (s, 3H), 2.31 (s, 3H), 2.01 (s, 6H); APCI MS m/z 426 [(M+H)$^+$, calcd for $C_{22}H_{24}N_3O_4S$, 426.1].

Example 4

[5-(4-Benzyloxybenzenesulfonyl)-2-methylpyrimidin-4-yl]-(2,4,6-trimethylphenyl)-amine

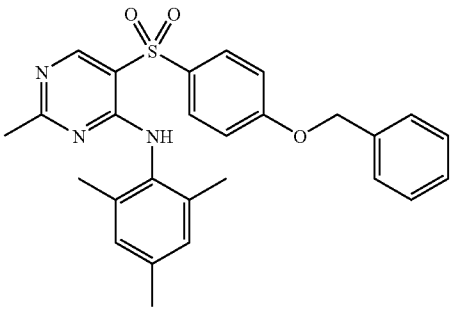

A mixture of 4-[2-methyl-4-(2,4,6-trimethylphenylamino)-pyrimidine-5-sulfonyl]-phenol (56 mg, 0.15 mmol), prepared as described in Example 2, potassium carbonate (40 mg, 29 mmol), benzyl bromide (0.034 mL, 0.29 mmol) and acetone (3 mL) was stirred at room temperature under N$_2$ for 48 h. The reaction mixture was diluted with water, and extracted (3×) with CH$_2$Cl$_2$. The combined organic layers were washed with brine, dried over Na$_2$SO$_4$, filtered and concentrated in vacuo. The residue was purified by chromatography on silica gel (50:50 hexanes/EtOAc) to provide the target compound (62 mg, 91%) as a white solid: mp 166–168° C.; $^1$H NMR (300 MHz, CDCl$_3$) δ 8.74 (s, 1H), 8.20 (br s, 1H), 7.87 (d, J=8.8 Hz, 2H), 7.36–7.40 (m, 5H), 7.05 (d, J=8.8 Hz, 2H), 6.91 (s, 2H), 5.12 (s, 2H), 2.39 (s, 3H), 2.31 (s, 3H), 2.00 (s, 6H); ESI MS m/z 474 [(M+H)$^+$, calcd for $C_{27}H_{28}N_3O_3S$, 474.2].

Example 5

[5-(4-Benzyloxybenzenesulfonyl)-2-methylpyrimidin-4-yl]-(4-methoxy-2-methylphenyl)-amine

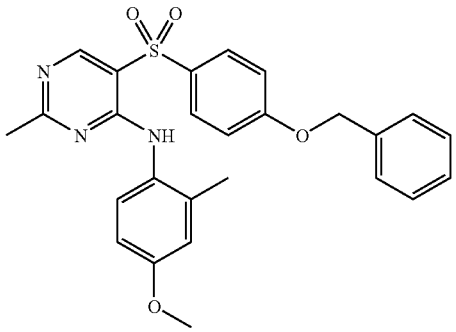

To a solution of 5-(4-benzyloxy-benzenesulfonyl)-4-chloro-2-methyl-pyrimidine (38 mg, 0.106 mmol) and 2-methyl-4-methoxy aniline (31 mg, 0.23 mmol) in toluene (1 mL) was added p-toluenesulfonic acid monohydrate (1.6 mg, 0.0081 mmol). The resulting mixture was heated at reflux under $N_2$ for 1 h and then cooled to room temperature. The mixture was quenched by addition of water, and extracted with EtOAc. The combined organic layers were washed with brine, dried over $Na_2SO_4$, filtered and concentrated in vacuo. The residue was purified using preparative TLC on silica (1:1 hexanes/EtOAc) to provide the desired product (46 mg, 95%) as a pale yellow solid: mp 110–114° C.; $^1$H NMR (500 MHz, CDCl$_3$) δ 8.71 (s, 1H), 8.61 (s, 1H), 7.86 (d, J=9.1 Hz, 2H), 7.49 (d, J=8.6 Hz, 1H), 7.38–7.33 (m, 4H), 7.07–7.04 (m, 2H), 6.79–6.75 (m, 2H), 5.12 (s, 2H), 3.81 (s, 3H), 2.46 (s, 3H), 2.17 (s, 3H); ESI MS m/z 476 [(M+H)$^+$, calcd for $C_{26}H_{26}N_3O_4S$, 476.2].

Example 6

[5-(4-Benzyloxybenzenesulfonyl)-2-methylpyrimidin-4-yl]-(6-methoxy-2-methylpyridin-3-yl)-amine

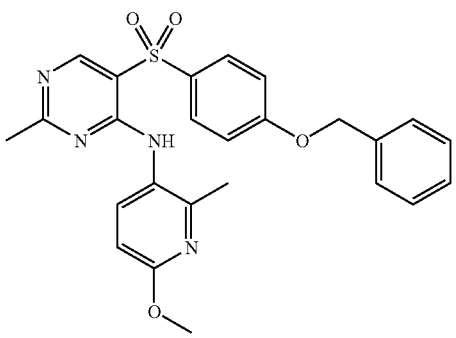

Prepared by the method described in Example 5 using the appropriate starting materials to give the desired product (14 mg, 11%) as a pink solid: mp 160–165° C.; $^1$H NMR (300 MHz, CDCl$_3$) δ 8.73 (s, 1H), 8.59 (s, 1H), 7.88 (d, J=8.8 Hz, 2H), 7.76 (d, J=8.7 Hz, 1H), 7.40 (s, 5H), 7.08 (d, J=8.9 Hz, 2H), 6.61 (d, J=8.7 Hz, 1H), 5.13 (s, 2H), 3.93 (s, 3H), 2.47 (s, 3H), 2.34 (s, 3H); APCI MS m/z 477 [(M+H)$^+$, calcd for $C_{25}H_{25}N_4O_4S$, 477.2].

Example 7

[5-(3-Benzyloxybenzenesulfonyl)-2-methylpyrimidin-4-yl]-(2,4,6-trimethylphenyl)-amine

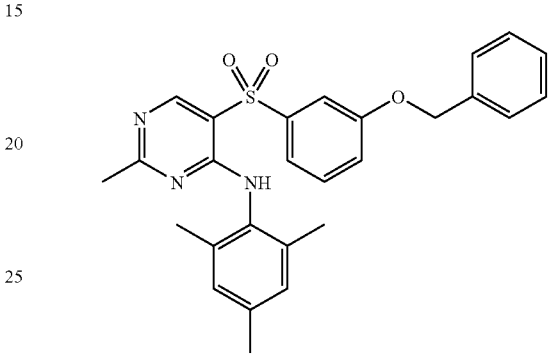

Prepared by the method described in Example 5 using the appropriate starting materials to give the desired product as a colorless solid: mp 112–115° C.; $^1$H NMR (300 MHz, CDCl$_3$) δ 8.75 (s, 1H), 8.17, (s, 1H), 7.19–7.55 (m, 9H), 6.92 (s, 2H), 5.09 (s, 2H), 2.04 (s, 3H), 2.31 (s, 3H), 2.00 (s, 6H); APCI MS m/z 474 [(M+H)$^+$, calcd for $C_{27}H_{28}N_3O_3S$, 474.2].

Example 8

[5-(3-Benzyloxybenzenesulfonyl)-2-methoxypyrimidin-4-yl]-(2,4,6-trimethylphenyl)-amine

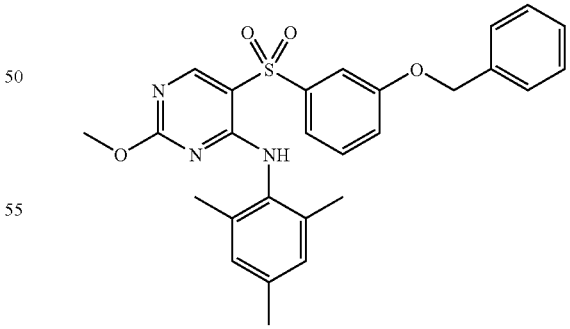

Prepared by the method described in Example 4 using the appropriate starting materials to give the desired product as an oil: $^1$H NMR (300 MHz, CDCl$_3$) δ 8.69 (s, 1H), 8.22, (s, 1H), 7.19–7.55 (m, 9H), 6.89 (s, 2H), 5.10 (s, 2H), 3.72 (s, 3H), 2.29 (s, 3H), 2.00 (s, 6H); APCI MS m/z 490 [(M+H)$^+$, calcd for $C_{27}H_{28}N_3O_4S$, 490.2].

Example 9

5-(3-Benzyloxybenzenesulfonyl)-N²,N²-dimethyl-N⁴-(2,4,6-trimethylphenyl)-pyrimidine-2,4-diamine

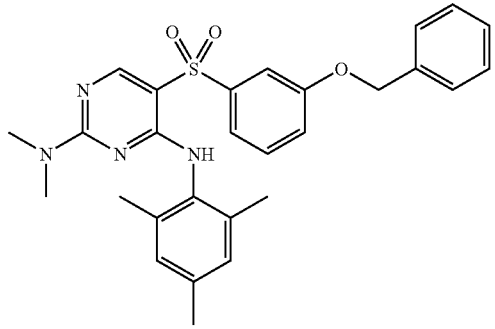

Prepared by the method described in Example 4 using the appropriate starting materials to give the desired product as a white solid: mp 52–58° C.; ¹H NMR (300 MHz, CDCl₃) δ 8.54 (s, 1H), 8.02, (s, 1H), 7.26–7.53 (m, 9H), 6.87 (s, 2H), 5.08 (s, 2H), 3.12 (s, 3H), 2.80 (s, 3H), 2.28 (s, 3H), 2.03 (s, 6H); APCI MS m/z 503 [C₂₈H₃₁N₄O₃S, 503.2].

Example 10

{5-[4-(2-Methoxybenzyloxy)-benzenesulfonyl]-2-methylpyrimidin-4-yl}-(2,4,6-trimethylphenyl)-amine

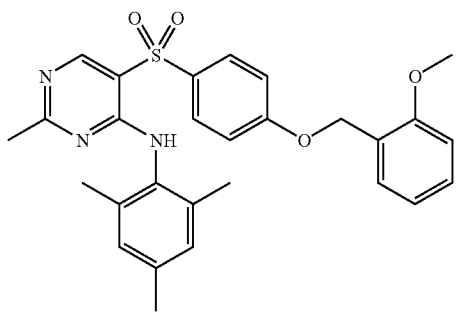

Prepared by the method described in Example 4 using the appropriate starting materials to give the desired product as a light yellow solid: mp 200–202° C.; ¹H NMR (300 MHz, CDCl₃) δ 8.74 (s, 1H), 8.20 (br s, 1H), 7.87 (d, J=8.8 Hz, 2H), 7.35 (m, 2H), 7.07 (d, J=8.8 Hz, 2H), 6.96 (m, 2H), 6.91 (s, 2H), 5.17 (s, 2H), 3.86 (s, 3H), 2.39 (s, 3H), 2.31 (s, 3H), 2.00 (s, 6H); APCI MS m/z 504 [(M+H)⁺, calcd for C₂₈H₃₀N₃O₄S, 504.2].

Example 11

{5-[4-(3,5-Dimethoxybenzyloxy)-benzenesulfonyl]-2-methylpyrimidin-4-yl}-(2,4,6-trimethylphenyl)-amine

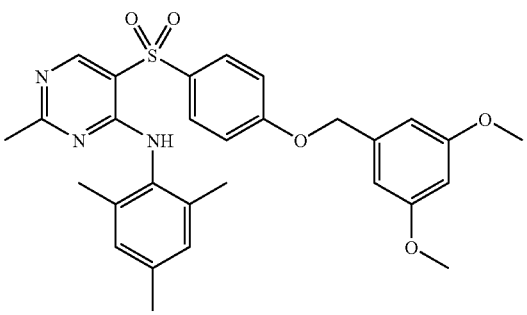

Prepared by the method described in Example 4 using the appropriate starting materials to give the desired product as a colorless oil: ¹H NMR (300 MHz, CDCl₃) δ 8.74 (s, 1H), 8.20 (br s, 1H), 7.87 (d, J=9.0 Hz, 2H), 7.05 (d, J=9.0 Hz, 2H), 6.91 (s, 2H), 6.53 (d, J=2.0 Hz, 2H), 6.42 (t, J=2.0 Hz, 1H), 5.06 (s, 2H), 3.79 (s, 3H), 2.39 (s, 3H), 2.31 (s, 3H), 2.00 (s, 6H); APCI MS m/z 534 [(M+H)⁺, calcd for C₂₉H₃₂N₃O₅S, 534.2].

Example 12

[5-(4-Benzyloxybenzenesulfonyl)-2-methylpyrimidin-4-yl]-(2,4-dimethoxyphenyl)-amine

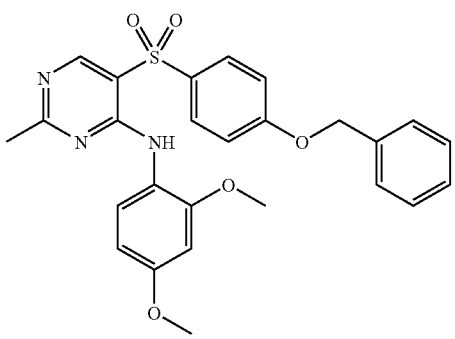

Prepared by the method described in Example 4 using the appropriate starting materials to give the desired product as a yellow solid: ¹H NMR (300 MHz, CDCl₃) δ 9.32 (s, 1H), 8.75 (s, 1H), 8.33 (d, J=8.7 Hz, 1H), 7.92 (d, J=8.3 Hz, 2H), 7.38 (s, 5H), 7.03 (d, J=8.4 Hz, 2H), 6.50–6.55 (m, 2H), 5.10 (s, 2H), 3.96 (s, 3H), 3.83 (s, 3H), 2.56 (s, 3H); ESI MS m/z 492 [(M+H)⁺, calcd for C₂₆H₂₆N₃O₅S, 492.2].

Example 13

5-(4-Methoxyoxybenzenesulfonyl)-2-methyl-4-(2,4,6-trimethylbenzyl)-pyrimidine

Part A. 5-(4-Methoxy-benzenesulfonyl)-2-methylpyrimidine

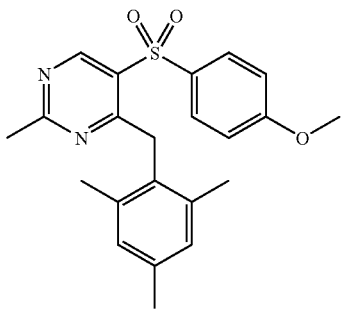

A mixture of 4-chloro-5-(4-methoxy-benzenesulfonyl)-2-methylpyrimidine (468 mg, 1.57 mmol), prepared by the method described in example 1 part E, 10% Pd/C (50 mg), NaOAc (128 mg, 1.57 mmol), ethanol (5 mL) and toluene (15 mL) was hydrogenated at 40 psi (Parr Shaker Apparatus) overnight. The mixture was filtered through a pad of silica gel, and washed with EtOAc. The filtrate was concentrated in vacuo and the residue was purified by chromatography on silica gel (67:33 hexanes/EtOAc) to provide 5-(4-methoxy-benzenesulfonyl)-2-methylpyrimidine (346 mg, 84%) as a white solid: $^1$H NMR (500 MHz, CDCl$_3$) δ 9.06 (s, 2H), 7.90 (d, J=9.9 Hz, 2H), 7.01 (d, J=9.9 Hz, 2H), 3.88 (s, 3H), 2.80 (s, 3H); ESI MS m/z 265 [(M+H)$^+$, calcd for C$_{12}$H$_{13}$N$_2$O$_3$S, 265.1].

Part B. 5-(4-Methoxy-benzenesulfonyl)-2-methyl-6-(2,4,6-trimethylbenzyl)-1,6-dihydro-pyrimidine To a mixture of magnesium (240 mg, 10 mmol) and ether (20 mL) was added 2,4,6-trimethylbenzyl chloride (1.69 g, 10 mmol) in ether (20 mL) dropwise at reflux under N$_2$. The freshly prepared solution of 2,4,6-trimethylbenzylmagnesium chloride in ether was added to a solution of 5-(4-methoxy-benzenesulfonyl)-2-methylpyrimidine (264 mg, 1.0 mmol) in THF (10 mL) dropwise at 0° C. The mixture was stirred under N$_2$ at 0° C. for 1 h and then quenched by addition of saturated aqueous NH$_4$Cl. The organic layer was separated and the aqueous layer was extracted three times with EtOAc. The combined organic layers were washed with brine, dried over Na$_2$SO$_4$, filtered and concentrated in vacuo. The residue was purified by chromatography on silica gel (EtOAc) to provide 5-(4-methoxy-benzenesulfonyl)-2-methyl-6-(2,4,6-trimethylbenzyl)-1,6-dihydro-pyrimidine (203 mg, 51%) as a light yellow solid: $^1$H NMR (500 MHz, CDCl$_3$) δ 7.86 (d, J=9.0 Hz, 2H), 7.45 (s, 1H), 6.99 (d, J=9.0 Hz, 2H), 6.83 (s, 2H), 4.40 (dd, J=10.8, 3.2 Hz, 1H), 3.86 (s, 3H), 2.96 (dd, J=14.2, 10.8 Hz, 1H), 2.87 (dd, J=14.2, 3.2 Hz, 1H), 2.25 (s, 6H), 2.24 (s, 3H), 1.91 (s, 3H); ESI MS m/z 399 [(M+H)$^+$, calcd for C$_{22}$H$_{27}$N$_2$O$_3$S, 399.2].

Part C. 5-(4-Methoxy-benzenesulfonyl)-2-methyl-4-(2,4,6-trimethylbenzyl)-pyrimidine A mixture 5-(4-methoxy-benzenesulfonyl)-2-methyl-6-(2,4,6-trimethylbenzyl)-1,6-dihydro-pyrimidine (167 mg, 0.42 mmol), NMO (74 mg, 0.63 mmol), TPAP (29 mg, 0.084 mmol), 4 Å molecular sieves (200 mg) and CH$_2$Cl$_2$ (5 mL) was stirred under N$_2$ at room temperature for 2 h. The mixture was filtered through a pad of silica gel and the filtrate was concentrated in vacuo. The residue was purified by chromatography on silica gel (67:33 hexanes/EtOAc) to provide the target compound (137 mg, 82%) as a light yellow solid: mp 150–152° C.; $^1$H NMR (500 MHz, CDCl$_3$) δ 9.22 (s, 1H), 7.93 (d, J=8.9 Hz, 2H), 7.06 (d, J=8.9 Hz, 2H), 6.83 (s, 2H), 4.25 (s, 2H), 3.91 (s, 3H), 2.59 (s, 3H), 2.29 (s, 3H), 1.91 (s, 6H); ESI MS m/z 397 [(M+H)$^+$, calcd for C$_{22}$H$_{25}$N$_2$O$_3$S, 397.2].

Example 14

5-(4-Benzyloxybenzenesulfonyl)-2-methyl-4-(2,4,6-trimethylbenzyl)-pyrimidine

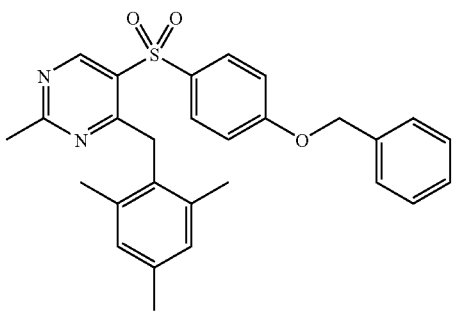

5-(4-Benzyloxy-benzenesulfonyl)-2-methyl-4-(2,4,6-trimethylbenzyl)-pyrimidine was prepared from 5-(4-methoxy-benzenesulfonyl)-2-methyl-4-(2,4,6-trimethylbenzyl)-pyrimidine by the method described in Examples 13 and 4 to provide the desired product as a white solid: mp 166–168° C.; $^1$H NMR (500 MHz, CDCl$_3$) δ 9.19 (s, 1H), 7.89 (d, J=8.9 Hz, 2H), 7.35–7.40 (m, 5H), 7.09 (d, J=8.9 Hz, 2H), 6.81 (s, 2H), 5.15 (s, 2H), 4.21 (s, 2H), 2.56 (s, 3H), 2.26 (s, 3H), 1.86 (s, 6H); ESI MS m/z 473 [(M+H)$^+$, calcd for C$_{28}$H$_{29}$N$_2$O$_3$S, 473.2].

Example 15

[5-(4-Fluorobenzenesulfonyl)-2-methylpyrimidin-4-yl]-(2,4,6-trimethylphenyl)-amine

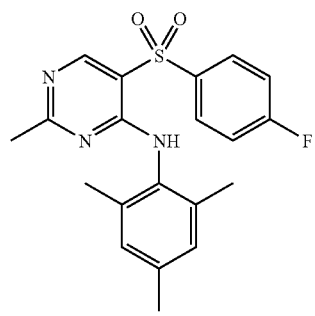

Prepared by the method described in Example 1 using 4-fluorothiophenol as the starting material to give the desired product as a light yellow solid: mp 191–193° C.; $^1$H NMR (300 MHz, CDCl$_3$) δ 8.76 (s, 1H), 8.20 (br s, 1H), 7.99 (dd, J=8.8, 5.0 Hz, 2H), 7.21 (d, J=8.8 Hz, 2H), 6.92 (s, 2H), 2.40 (s, 3H), 2.31 (s, 3H), 2.01 (s, 6H); ESI MS m/z 386 [(M+H)$^+$, calcd for C$_{20}$H$_{21}$FN$_3$O$_2$S, 386.1].

Example 16

[2-Methyl-5-(4-morpholin-4-yl-benzenesulfonyl)-pyrimidin-4-yl]-(2,4,6-trimethylphenyl)-amine

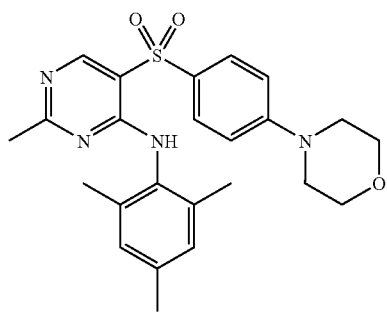

A mixture of [5-(4-fluoro-benzenesulfonyl)-2-methyl-pyrimidin-4-yl]-(2,4,6-trimethylphenyl)-amine (100 mg, 0.26 mmol) and morpholine (5 mL) was heated at reflux under $N_2$ for 2 h, and then cooled to room temperature. The mixture was concentrated in vacuo, and the residue was dissolved in EtOAc, washed with water and brine, dried over $Na_2SO_4$, filtered and concentrated in vacuo. The residue was purified by chromatography on silica gel (EtOAc) to provide the target compound (108 mg, 92%) as a white solid: mp 221–223° C.; $^1$H NMR (500 MHz, CDCl$_3$) δ 8.71 (s, 1H), 8.24 (br s, 1H), 7.80 (d, J=9.0 Hz, 2H), 6.91 (s, 2H), 6.88 (d, J=9.0 Hz, 2H), 3.83 (t, J=5.0 Hz, 4H), 3.29 (t, J=5.0 Hz, 4H), 2.37 (s, 3H), 2.30 (s, 3H), 2.03 (s, 6H); APCI MS m/z 453 [(M+H)$^+$, calcd for $C_{24}H_{29}N_4O_3S$, 453.2].

Example 17

{2-Methyl-5-[4-(4-methylpiperazin-1-yl)-benzenesulfonyl]-pyrimidin-4-yl}-(2,4,6-trimethylphenyl)-amine

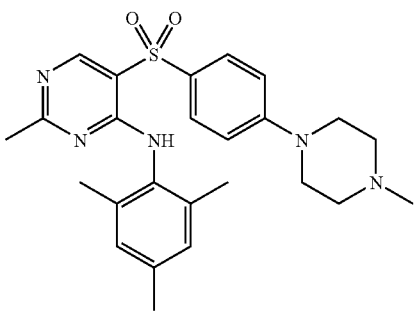

Prepared by the method described in Example 16 using the appropriate starting materials to give the desired product as a colorless oil: $^1$H NMR (300 MHz, CDCl$_3$) δ 8.72 (s, 1H), 8.24 (br s, 1H), 7.78 (d, J=9.0 Hz, 2H), 6.91 (s, 2H), 6.88 (d, J=9.0 Hz, 2H), 3.35 (t, J=5.0 Hz, 4H), 2.53 (t, J=5.0 Hz, 4H), 2.39 (s, 3H), 2.34 (s, 3H), 2.31 (s, 3H), 2.03 (s, 6H); APCI MS m/z 466 [(M+H)$^+$, calcd for $C_{25}H_{32}N_5O_2S$, 466.2].

Example 18

[5-(4-Imidazol-1-yl-benzenesulfonyl)-2-methylpyrimidin-4-yl]-(2,4,6-trimethylphenyl)-amine

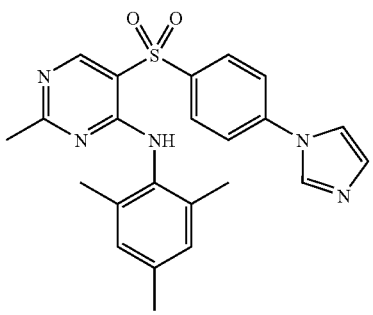

Sodium hydride (60% in oil, 32 mg, 0.78 mmol) was added to a solution of [5-(4-fluoro-benzenesulfonyl)-2-methylpyrimidin-4-yl]-(2,4,6-trimethylphenyl)-amine (100 mg, 0.26 mmol) and imidazole (53 mg, 0.78 mmol) in 1,4-dioxane (4 mL). The mixture was stirred at room temperature for 10 min and then heated at reflux under $N_2$ for 24 h. The mixture was cooled to room temperature, and saturated aqueous $NH_4Cl$ was added. The mixture was extracted three times with $CH_2Cl_2$, and the combined organic layers were washed with brine, dried over $Na_2SO_4$, filtered and concentrated in vacuo. The residue was purified by chromatography on silica gel (EtOAc) to provide the target compound (56 mg, 50%) as a white solid: mp 230–232° C.; $^1$H NMR (500 MHz, DMSO-d$_6$) δ 8.82 (s, 1H), 8.48 (br s, 1H), 8.44 (s, 1H), 8.34 (d, J=8.7 Hz, 2H), 7.95 (d, J=8.7 Hz, 2H), 7.90 (s, 1H), 7.15 (s, 1H), 6.89 (s, 2H), 2.25 (s, 3H), 2.24 (s, 3H), 1.86 (s, 6H); APCI MS m/z 434 [(M+H)$^+$, calcd for $C_{23}H_{24}N_5O_2S$, 434.1].

Example 19

[2-Methyl-5-(4-pyrrolidin-1-yl-benzenesulfonyl)-pyrimidin-4-yl]-(2,4,6-trimethylphenyl)-amine

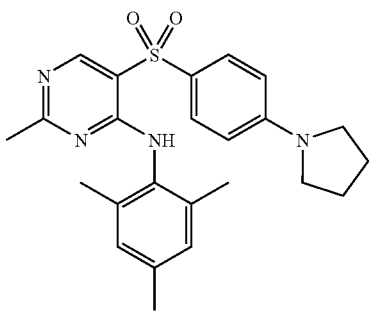

Prepared by the method described in Example 16 using the appropriate starting materials to give the desired product as a light yellow solid: mp 196–198° C.; $^1$H NMR (300 MHz, CDCl$_3$) δ 8.71 (s, 1H), 8.28 (br s, 1H), 7.74 (d, J=9.0 Hz, 2H), 6.91 (s, 2H), 6.52 (d, J=9.0 Hz, 2H), 3.33 (t, J=6.5 Hz, 4H), 2.37 (s, 3H), 2.30 (s, 3H), 2.04 (t, J=6.5 Hz, 4H), 2.04 (s, 6H); ESI MS m/z 437 [(M+H)$^+$, calcd for $C_{24}H_{29}N_4O_2S$, 437.2].

Example 20

[5-(4-Benzylaminobenzenesulfonyl)-2-methylpyrimidin-4-yl]-(2,4,6-trimethylphenyl)-amine

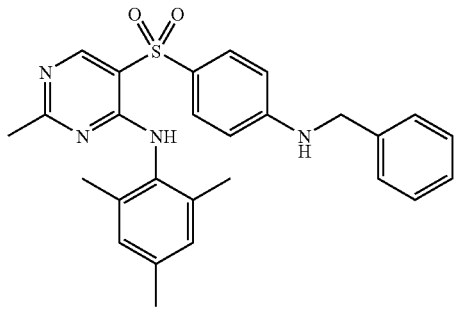

Prepared by the method described in Example 16 using the appropriate starting materials to give the desired product as a white solid: mp 200–202° C.; $^1$H NMR (300 MHz, CDCl$_3$) δ 8.71 (s, 1H), 8.21 (br s, 1H), 7.77 (d, J=8.9 Hz, 2H), 7.31 (m, 5H), 6.91 (s, 2H), 6.62 (d, J=8.9 Hz, 2H), 4.73 (t, J=5.5 Hz, 1H), 4.38 (d, J=5.5 Hz, 2H), 2.38 (s, 3H), 2.30 (s, 3H), 2.01 (s, 6H); APCI MS m/z 473 [(M+H)$^+$, calcd for C$_{27}$H$_{29}$N$_4$O$_2$S, 473.2].

Example 21

{5-[4-(Benzylmethylamino)-benzenesulfonyl]-2-methylpyrimidin-4-yl}-(2,4,6-trimethylphenyl)-amine

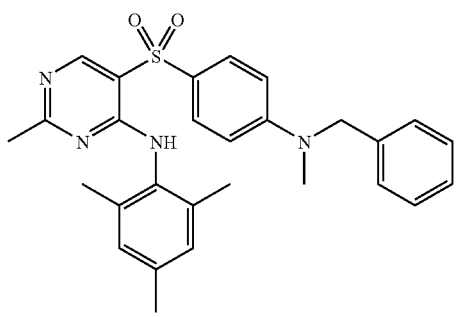

Prepared by the method described in Example 16 using the appropriate starting materials to give the desired product as a white solid: mp 146–148° C.; $^1$H NMR (300 MHz, CDCl$_3$) δ 8.71 (s, 1H), 8.21 (br s, 1H), 7.73 (d, J=9.2 Hz, 2H), 7.32 (m, 3H), 7.12 (m, 2H), 6.91 (s, 2H), 6.71 (d, J=9.2 Hz, 2H), 4.62 (s, 2H), 3.13 (s, 3H), 2.38 (s, 3H), 2.30 (s, 3H), 2.01 (s, 6H); APCI MS m/z 487 [(M+H)$^+$, calcd for C$_{28}$H$_{31}$N$_4$O$_2$S, 487.2].

Example 22

4-[2-Methyl-4-(2,4,6-trimethylphenylamino)-pyrimidine-5-sulfonyl]-benzonitrile

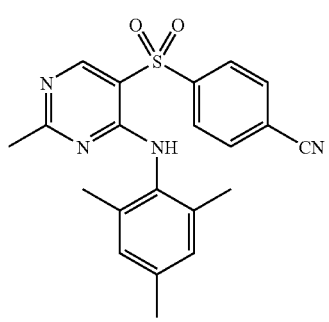

Part A. Trifluoromethanesulfonic acid 4-[2-methyl-4-(2,4,6-trimethylphenylamino)-pyrimidine-5-sulfonyl]-phenyl ester To a solution of 4-[2-methyl-4-(2,4,6-trimethyl-phenylamino)-pyrimidine-5-sulfonyl]-phenol (122 mg, 0.318 mmol), prepared by the method described in Example 2, and triethylamine (0.053 mL, 0.38 mmol) in CH$_2$Cl$_2$ (3 mL) was added trifluoromethanesulfonyl chloride (0.037 mL, 0.35 mmol) at 0° C. The reaction mixture was stirred under N$_2$ and slowly warmed to room temperature. The mixture was treated with saturated aqueous NaHCO$_3$, and extracted (3×) with CH$_2$Cl$_2$. The combined organic layers were washed with brine, dried over Na$_2$SO$_4$, filtered and concentrated in vacuo. The residue was purified by chromatography on silica gel (67:33 hexanes/EtOAc) to provide trifluoromethanesulfonic acid 4-[2-methyl-4-(2,4,6-trimethylphenylamino)-pyrimidine-5-sulfonyl]-phenyl ester (150 mg, 91%) as a white solid: $^1$H NMR (300 MHz, CDCl$_3$) δ 8.79 (s, 1H), 8.15 (br s, 1H), 8.08 (d, J=8.9 Hz, 2H), 7.47 (d, J=8.9 Hz, 2H), 6.92 (s, 2H), 2.42 (s, 3H), 2.31 (s, 3H), 1.98 (s, 6H); ESI MS m/z 516 [(M+H)$^+$, calcd for C$_{21}$H$_{21}$F$_3$N$_3$O$_5$S$_2$, 516.1].

Part B. 4-[2-Methyl-4-(2,4,6-trimethylphenylamino)-pyrimidine-5-sulfonyl]-benzonitrile A mixture of trifluoromethanesulfonic acid 4-[2-methyl-4-(2,4,6-trimethylphenylamino)-pyrimidine-5-sulfonyl]-phenyl ester (146 mg, 0.283 mmol), zinc cyanide (66 mg, 0.57 mmol), and DMF (2 mL) was degassed with N$_2$ for 10 min, and then Pd(PPh$_3$)$_4$ (16 mg, 0.014 mmol) was added. The mixture was stirred at 80° C. under N$_2$ for 2 h and then cooled to room temperature. The reaction mixture was treated with saturated aqueous NaHCO$_3$, and extracted (3×) with EtOAc. The combined organic layers were washed with brine, dried over Na$_2$SO$_4$, filtered and concentrated in vacuo. The residue was purified by chromatography on silica gel (67:33 hexanes/EtOAc) to provide the target compound (108 mg, 97%) as a white solid: mp 258–260° C.; $^1$H NMR (500 MHz, CDCl$_3$) δ 8.76 (s, 1H), 8.21 (br s, 1H), 8.08 (d, J=8.6 Hz, 2H), 7.84 (d, J=8.6 Hz, 2H), 6.92 (s, 2H), 2.40 (s, 3H), 2.31 (s, 3H), 2.00 (s, 6H); ESI MS m/z 393 [(M+H)$^+$, calcd for C$_{21}$H$_{21}$N$_4$O$_2$S, 393.1].

Example 23

[2-Methyl-5-(toluene-4-sulfonyl)-pyrimidin-4-yl]-(2,4,6-trimethylphenyl)-amine

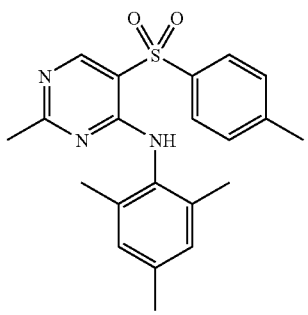

A mixture of trifluoromethanesulfonic acid 4-[2-methyl-4-(2,4,6-trimethylphenylamino)-pyrimidine-5-sulfonyl]-phenyl ester (158 mg, 0.306 mmol), prepared by the method described in Example 22, methylboronic acid (36 mg, 0.61 mmol), 2 M $Na_2CO_3$ (2.0 mL, 4.0 mmol), and DME (4 mL) was degassed with $N_2$ for 10 min, and then $PdCl_2(PPh_3)_2$ (43 mg, 0.061 mmol) and triphenylphosphine (32 mg, 0.12 mmol) were added. The mixture was refluxed under $N_2$ for 2 h and then cooled to room temperature. The reaction mixture was diluted with water, and extracted (3×) with EtOAc. The combined organic layers were washed with brine, dried over $Na_2SO_4$, filtered and concentrated in vacuo. The residue was purified by chromatography on silica gel (67:33 hexanes/EtOAc) to provide the desired product (76 mg, 65%) as a white solid: mp 202–204° C.; $^1$H NMR (300 MHz, $CDCl_3$) δ 8.75 (s, 1H), 8.23 (br s, 1H), 7.84 (d, J=8.4 Hz, 2H), 7.33 (d, J=8.4 Hz, 2H), 6.91 (s, 2H), 2.43 (s, 3H), 2.38 (s, 3H), 2.30 (s, 3H), 2.00 (s, 6H); ESI MS m/z 382 [(M+H)$^+$, calcd for $C_{21}H_{24}N_3O_2S$, 382.2].

Example 24

[2-Methyl-5-(4-pyrimidin-5-yl-benzenesulfonyl)-pyrimidin-4-yl]-(2,4,6-trimethylphenyl)-amine

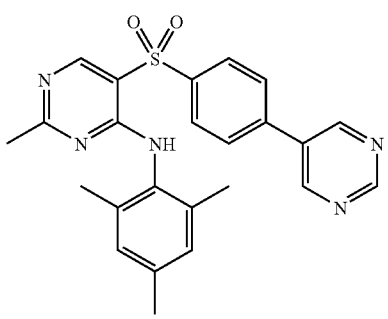

A mixture of trifluoromethanesulfonic acid 4-[2-methyl-4-(2,4,6-trimethylphenylamino)-pyrimidine-5-sulfonyl]-phenyl ester (95 mg, 0.18 mmol), prepared by the method described in Example 22, 5-tributylstannanyl-pyrimidine (75 mg, 0.20 mmol), LiCl (23 mg, 0.55 mmol) and DMF (4 mL) was deoxygenated with $N_2$ for 10 min, and then $Pd(PPh_3)_2Cl_2$ (13 mg, 0.018 mmol) and $PPh_3$ (10 mg, 0.036 mmol) were added. The mixture was heated at 150° C. under $N_2$ for 2 h and then cooled to room temperature. Saturated aqueous KF was added, and the mixture was extracted three times with $CH_2Cl_2$. The combined organic layers were washed with brine, dried over $Na_2SO_4$, filtered and concentrated in vacuo. The residue was purified by chromatography on silica gel (50:50 hexanes/EtOAc) to provide the target compound (66 mg, 80%) as a white solid: mp 210–212° C.; $^1$H NMR (300 MHz, $CDCl_3$) δ 9.29 (s, 1H), 8.96 (s, 1H), 8.80 (s, 1H), 8.30 (br s, 1H), 8.13 (d, J=8.5 Hz, 2H), 7.76 (d, J=8.5 Hz, 2H), 6.93 (s, 2H), 2.41 (s, 3H), 2.31 (s, 3H), 2.03 (s, 6H); APCI MS m/z 446 [(M+H)$^+$, calcd for $C_{24}H_{24}N_5O_2S$, 446.2].

Example 25

[2-Methyl-5-(4-pyrimidin-2-yl-benzenesulfonyl)-pyrimidin-4-yl]-(2,4,6-trimethylphenyl)-amine

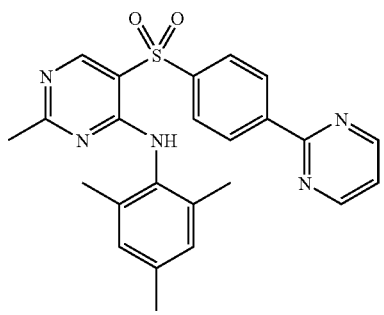

Prepared by the method described in Example 24 using the appropriate starting materials to give the desired product as a white solid: mp 215–217° C.; $^1$H NMR (300 MHz, $CDCl_3$) δ 8.85 (d, J=5.0 Hz, 2H), 8.81 (s, 1H), 8.65 (d, J=8.5 Hz, 2H), 8.31 (br s, 1H), 8.08 (d, J=8.5 Hz, 2H), 7.27 (t, J=5.0 Hz, 1H), 6.91 (s, 2H), 2.40 (s, 3H), 2.31 (s, 3H), 2.03 (s, 6H); ESI MS m/z 446 [(M+H)$^+$, calcd for $C_{24}H_{24}N_5O_2S$, 446.2].

Example 26

[2-Methyl-5-(4-pyridin-4-yl-benzenesulfonyl)-pyrimidin-4-yl]-(2,4,6-trimethylphenyl)-amine

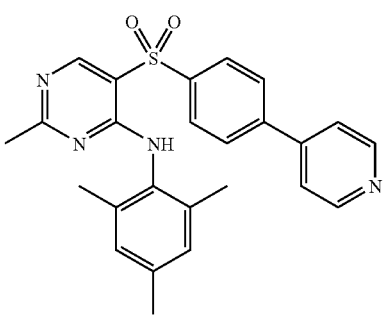

A mixture trifluoromethanesulfonic acid 4-[2-methyl-4-(2,4,6-trimethylphenylamino)-pyrimidine-5-sulfonyl]-phenyl ester (72 mg, 0.14 mmol), prepared by the method described in Example 22, pyridine-4-boronic acid (34 mg, 0.28 mmol), 2 M Na$_2$CO$_3$ (1.0 mL, 2.0 mmol) and DME (2 mL) was deoxygenated with N$_2$ for 10 min, and then Pd(PPh$_3$)$_2$Cl$_2$ (20 mg, 0.028 mmol) and PPh$_3$ (15 mg, 0.056 mmol) were added. The mixture was heated at reflux under N$_2$ for 2 h and then cooled to room temperature. Saturated aqueous NaHCO$_3$ was added, and the mixture was extracted three times with EtOAc. The combined organic layers were washed with brine, dried over Na$_2$SO$_4$, filtered and concentrated in vacuo. The residue was purified by chromatography on silica gel (50:50 hexanes/EtOAc) to provide the desired product (38 mg, 61%) as a white solid: mp 232–234° C.; $^1$H NMR (500 MHz, CDCl$_3$) δ 8.79 (s, 1H), 8.73 (d, J=4.5 Hz, 2H), 8.28 (br s, 1H), 8.13 (d, J=8.4 Hz, 2H), 7.78 (d, J=8.4 Hz, 2H), 7.48 (d, J=4.5 Hz, 2H), 6.92 (s, 2H), 2.40 (s, 3H), 2.31 (s, 3H), 2.03 (s, 6H); APCI MS m/z 445 [(M+H)$^+$, calcd for C$_{25}$H$_{25}$N$_4$O$_2$S, 445.2].

Example 27

[2-Methyl-5-(4-pyridin-2-yl-benzenesulfonyl)-pyrimidin-4-yl]-(2,4,6-trimethylphenyl)-amine

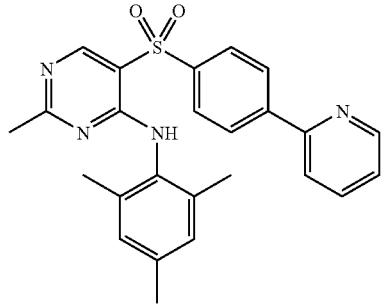

Prepared by the method described in Example 24 using the appropriate starting materials to give the desired product as a white solid: mp 201–203° C.; $^1$H NMR (500 MHz, CDCl$_3$) δ 8.79 (s, 1H), 8.72 (d, J=5.2 Hz, 1H), 8.30 (br s, 1H), 8.18 (d, J=8.8 Hz, 2H), 8.05 (d, J=8.8 Hz, 2H), 7.76–7.80 (m, 2H), 7.31 (m, 1H), 6.91 (s, 2H), 2.40 (s, 3H), 2.30 (s, 3H), 2.03 (s, 6H); APCI MS m/z 445 [(M+H)$^+$, calcd for C$_{25}$H$_{25}$N$_4$O$_2$S, 445.2].

Example 28

[2-Methyl-5-(4-pyridin-3-yl-benzenesulfonyl)-pyrimidin-4-yl]-(2,4,6-trimethylphenyl)-amine

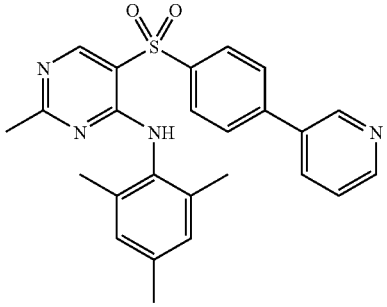

Prepared by the method described in Example 26 using the appropriate starting materials to give the desired product as a white solid: mp 190–192° C.; $^1$H NMR (500 MHz, CDCl$_3$) δ 8.84 (d, J=2.2 Hz, 1H), 8.79 (s, 1H), 8.67 (d, J=4.8 Hz, 1H), 8.27 (br s, 1H), 8.07 (d, J=8.5 Hz, 2H), 7.87 (dd, J=7.8, 3.8 Hz, 1H), 7.74 (d, J=8.5 Hz, 2H), 7.41 (dd, J=7.8, 4.8 Hz, 1H), 6.92 (s, 2H), 2.40 (s, 3H), 2.31 (s, 3H), 2.03 (s, 6H); ESI MS m/z 445 [(M+H)$^+$, calcd for C$_{25}$H$_{25}$N$_4$O$_2$S, 445.2].

Example 29

{5-[4-(4,5-Dihydro-1H-imidazol-2-yl)-benzenesulfonyl]-2-methyl-pyrimidin-4-yl}-(2,4,6-trimethylphenyl)-amine

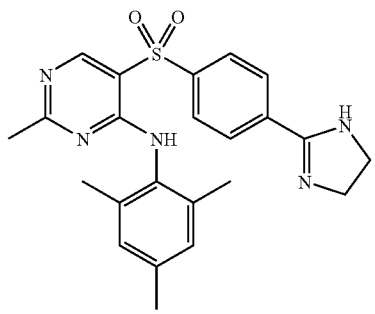

A mixture of 4-[2-methyl-4-(2,4,6-trimethyl-phenylamino)-pyrimidine-5-sulfonyl]-benzonitrile (83 mg, 0.21 mmol), prepared by the method described in Example 22, ethylenediamine (0.042 mL, 0.63 mmol), p-TsOH.H$_2$O (59 mg, 0.31 mmol) and toluene (4 mL) was heated at reflux under N$_2$ overnight and then cooled to room temperature. Saturated aqueous NaHCO$_3$ was added, and the mixture was extracted three times with EtOAc. The combined organic layers were washed with brine, dried over Na$_2$SO$_4$, filtered and concentrated in vacuo. The residue was purified by chromatography on silica gel (75:25 EtOAc/MeOH) to provide the target compound (14 mg, 15%) as a white solid: mp 240–242° C.; $^1$H NMR (300 MHz, CDCl$_3$) δ 8.78 (s, 1H), 8.27 (br s, 1H), 8.00 (d, J=8.5 Hz, 2H), 7.95 (d, J=8.5 Hz, 2H), 6.92 (s, 2H), 4.80 (br s, 1H), 3.83 (s, 4H), 2.40 (s, 3H), 2.30 (s, 3H), 2.01 (s, 6H); ESI MS m/z 436 [(M+H)$^+$, calcd for C$_{23}$H$_{26}$N$_5$O$_2$S, 436.2].

Example 30

{5-[4-(1H-Imidazol-2-yl)-benzenesulfonyl]-2-methyl-pyrimidin-4-yl}-(2,4,6-trimethylphenyl)-amine

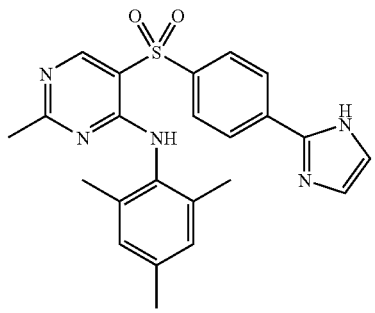

A mixture of {5-[4-(4,5-dihydro-1H-imidazol-2-yl)-benzenesulfonyl]-2-methyl-pyrimidin-4-yl}-(2,4,6-trimethylphenyl)-amine (14 mg, 0.032 mmol), prepared by the method described in Example 29, NMO (5.6 mg, 0.048 mmol), TPAP (2.2 mg, 0.006 mmol), 4 Å molecular sieves (100 mg) and CH$_2$Cl$_2$ (2 mL) was stirred under N$_2$ at room temperature for 10 min, and then filtered through a pad of silica gel. The filtrate was concentrated in vacuo, and the residue was purified by chromatography on silica gel (EtOAc) to provide the target compound (5 mg, 36%) as a white solid: mp 282–284° C.; $^1$H NMR (500 MHz, CDCl$_3$) δ 9.54 (br s, 1H), 8.78 (s, 1H), 8.27 (br s, 1H), 8.02 (d, J=8.5 Hz, 2H), 7.99 (d, J=8.5 Hz, 2H), 7.28 (s, 1H), 7.18 (s, 1H), 6.91 (s, 2H), 2.40 (s, 3H), 2.30 (s, 3H), 2.02 (s, 6H); ESI MS m/z 434 [(M+H)$^+$, calcd for C$_{23}$H$_{24}$N$_5$O$_2$S, 434.2].

Utility

CRF-R1 Receptor Binding Assay for the Evaluation of Biological Activity

The following is a description of the isolation of cell membranes containing cloned human CRF-R1 receptors for use in a standard binding assay as well as a description of the assay itself.

Messenger RNA was isolated from human hippocampus. The mRNA was isolated from human hippocampus. The mRNA was reverse transcribed using oligo (dt) 12–18 and the coding region was amplifies by PCR from start to stop codons. The resulting PCR fragment was cloned into the EcORV site of pGEMV, from whence the insert was reclaimed using XhoI+XbaI and cloned into the XhoI+XbaI sites of vector pm3as (which contains a CMV promoter, the SV't' splice and early poly A signals, an Eptein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately 1×10$^8$ of the suspended cells were then centrifuged to form a pellet and frozen. For the binding assay a frozen pellet described above containing 293EBNA cells transfected with hCRFR1 receptors is homogenized in 10 mL of ice cold tissue buffer (50 mM HEPES buffer pH 7.0, containing 10 MM MgCl$_2$, 2 mM EGTA, 1 μg/mL apotinin, 1 μg/mL leupeptin and 1 μg/mL pepstatin). The homoginate is centrifuged at 40,000×g for 12 min and the resulting pellet rehomogenized in 10 mL of tissue buffer. After another centrifugation at 40,000×g for 12 min, the pellet is resuspended to a protein concentration of 360 μg/mL to be used in the assay.

Binding assays are performed in 96 well plates; each well having a 300 μL capacity. To each well is added 50 μL of test drug dilutions (final concentration of drugs range from 10$^{-10}$–10$^{-5}$ M), 100 μL of $^{125}$I-ovine-CRF ($^{125}$I-o-CRF) (final concentration 150 pM) and 150 μL of the cell homoginate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.*, 107:220 (1980), which provides K$_i$ values for inhibition which are then used to assess biological activity.

A compound is considered to be active if it has a K$_i$ value of less than about 10,000 nM for the inhibition of CRF. Preferred compounds have a K$_i$ value of less than about 1000 nM for the inhibition of CRF. More preferred compounds have a K$_i$ values of less than about 100 nM for the inhibition of CRF.

Compounds of the present invention have demonstrated a K$_i$ value of less than about 10,000 nM for the inhibition of CRF in the CRF-R1 Receptor Binding Assay for the evaluation of biological activity.

Alternate CRF-R1 Receptor Binding Assay for the Evaluation of Biological Activity.

The following is a description of the isolation of cell membranes containing cloned human CRF-R1 receptors for use in a standard binding assay as well as a description of the assay itself.

Messenger RNA was isolated from human hippocampus. The mRNA was isolated from human hippocampus. The mRNA was reverse transcribed using oligo (dt) 12–18 and the coding region was amplifies by PCR from start to stop codons. The resulting PCR fragment was cloned into the EcORV site of pGEMV, from whence the insert was reclaimed using XhoI+XbaI and cloned into the XhoI+XbaI sites of vector pm3as (which contains a CMV promoter, the SV't' splice and early poly A signals, an Eptein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below.

HEK 293 EBNA-1 cells (HEK 293E, Invitrogen, CA), were transfected with a vector encoding the human CRF-R1 gene using a standard calcium phosphate protocol. The vector sequence included the oriP origin of replication, which permits episomal maintenance in cells expressing the EBNA-1 gene, and the gene for hygromycin resistance. Following transfection, cells were pooled and plated into a medium containing hygromycin for the selection of cells expressing CRF-R1. After isolation, the cell pool CL0138 was assessed in radioligand binding and functional-based assays. These cells are maintained in Dulbecco's Modified Eagle medium (DMEM) containing 10% v/v fetal bovine serum (FBS), 2 mM L-glutamine and 400 μg/mL hygromycin. Cell pellets prepared from this cell line were used in CRF$_1$ competition binding assays. Individual aliquots containing approximately 1×10$^8$ of the suspended cells were then centrifuged to form a pellet, frozen and stored at −80° C.

A frozen pellet described above containing 293EBNA cells transfected with hCRFR1 receptors or the rat frontal cortex tissue dissected from frozen rat brains was prepared as the source of membranes expressing CRF1 receptors used in binding assays. Tissue or pellets of whole cells were thawed on ice and homogenized in tissue buffer (containing 50 mM HEPES, 10 mM MgCl$_2$, 2 mM EGTA, and 1 μg/mL each of aprotonin, leupeptin, and pepstatin, pH 7.0 @ 23° C.) using a Brinkman Polytron (PT-10, setting 6 for 10 seconds). The homogenate was centrifuged at 48,000×g for 12 min and the resulting pellet was washed by double re-suspension and centrifugation steps. Membranes from rat frontal cortex were prepared similarly except for the inclusion of an additional wash/centrifugation cycle. The final pellet was suspended in tissue buffer, and protein concentrations were determined using the bicinchoninic acid (BCA) assay (Pierce, Rockford, Ill.) with bovine serum albumin as standard.

Equilibrium competition binding experiments were performed using a modification of the methods described previously to determine binding affinities of compounds at $CRF_1$ (Arvanitis et al., 1999). All small molecule ligands were initially prepared in 100% DMSO at a concentration of $10^{-2}$ M and diluted in assay buffer that was identical to the tissue buffer except for the inclusion of 0.15 mM bacitracin and 0.1% w/v ovalbumin. Competition assays were conducted in disposable polypropylene 96-well plates (Costar Corp., Cambridge, Mass.), in a total volume of 300 µL. The reaction was initiated by the addition of 50 µL of competing compounds in 12 concentrations (final concentrations ranging from $10^{-11}$ to $10^{-5}$ M), 100 µL assay buffer containing the radioligand $[^{125}I]$ovine CRF (final concentration 150 pM), and 150 µL membrane homogenate (containing 5–10 µg protein). The reaction mixtures were incubated to equilibrium for 2 h at 23° C. Specific binding was defined in the presence of 10 µM DMP 696 or SC241 for $CRF_1$ receptors. Binding assays were terminated by rapid filtration over GF/C glass-fibers (pre-soaked in 0.3% v/v polyethyleneimine) using a 96-well cell harvester followed by three washes with 0.3 mL cold wash buffer (PBS, pH 7.0, containing 0.01% Triton X-100). The filter was dried, and counted in a gamma counter or a 96-well Top Counter at 80% efficiency. The $CRF_1$ competition binding to membranes from rat frontal cortex were performed similarly except for the radioligand concentration of $[^{125}I]$ovine (final concentration approximately 200 pM) and membrane protein (40–65 µg/well) used in the binding.

The inhibition of $[^{125}I]$ovine CRF binding to cell membranes by increasing concentrations of test drugs are analyzed by fitting data through the competition equation in the iterative nonlinear regression curve-fitting programs Prism (GraphPad Prism, San Diego, Calif.) to determine binding affinities ($IC_{50}$'s or $K_i$'s) of ligands for $CRF_1$ receptors. A compound is considered to be active if it has a $K_i$ value of less than about 10,000 nM for the inhibition of $[^{125}I]$ovine CRF binding.

Inhibition of CRF-Stimulated Adenylate Cyclase Activity

Inhibition of CRF-stimulated adenylate cyclase activity can be performed as described by G. Battaglia et al., *Synapse*, 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions are initiated by the addition of 1 mM ATP/$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of $[^{3}H]$cAMP (approximately 40,000 dpm) is added to each tube prior to separation. The separation of $[^{32}P]$cAMP from $[^{32}P]$ATP is performed by sequential elution over Dowex and alumina columns.

In vivo Biological Assay

The in vivo activity of the compounds of the present invention can be assessed using any one of the biological assays available and accepted within the art. Illustrative of these tests includes the Acoustic Startle Assay, the Stair Climbing Test, and the Chronic Administration Assay. These and other models useful for the testing of compounds of the present invention have been outlined in C. W. Berridge and A. J. Dunn, *Brain Research Reviews*, 15:71 (1990). Compounds may be tested in any species of rodent or small mammal.

Compounds of this invention have utility in the treatment of imbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Suitable pharmaceutical carriers are described in *Remington's Pharmaceutical Sciences*, A. Osol, a standard reference in the field.

The compounds of this invention may also be used as reagents or standards in the biochemical study of neurological function, dysfunction, and disease.

Although the present invention has been described and exemplified in terms of certain particular embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formula (I)

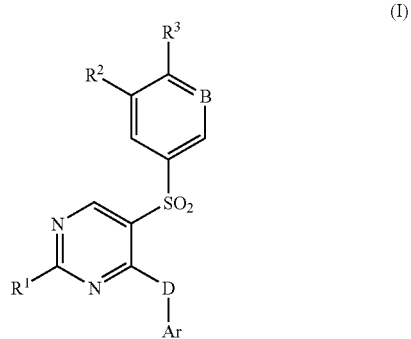

or pharmaceutically acceptable salt thereof, wherein
B is CH or N;
D is $CH_2$ or NH;
$R^1$ is selected from the group consisting of H, —CN, $C_{1-4}$ alkyl, $C_{3-7}$ cycloalkyl, $C_{2-4}$ alkenyl, $C_{2-4}$ alkynyl, $C_{1-4}$ alkoxy and $N(C_{1-4}$ alkyl$)_2$ optionally and independently substituted with 1 to 3 substituents selected from the group consisting of —CN, hydroxy, halo, $C_{1-4}$ haloalkyl and $C_{1-4}$ alkoxy;
$R^2$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —$NR^4R^6$, —$C_{1-6}$alkyl$NR^4R^6$, —$C_{1-6}$alkyl$OR^6$, $CO_2R^6$, $O_2CR^6$, $COR^6$, $CON^4R^6$, $NR^4CO_2R^6$, $NR^4SO_2R^6$, $NR^4COR^6$, $OCONR^4R^6$ and $NR^4CONR^5R^6$;
   optionally and independently substituted with 1 to 3 substituents selected from the group consisting of —CN, hydroxy, halo, $C_{1-4}$ haloalkyl, $C_{1-4}$ alkoxy, $CO_2C_{1-4}$ alkyl or phenyl; or
$R^2$ is morpholinyl, thiomorpholinyl, piperadinyl, piperazinyl, phenyl, pyridyl, pyrimidinyl, triazinyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl and indazolyl, independently and optionally substituted with 1 to 4 substituents selected from the group consisting of H, $C_{1-6}$ alkyl, $C_{1-4}$ alkoxy-$C_{1-4}$ alkyl, $C_{3-6}$ cycloalkyl, —$OR^4$, halo, $C_{1-6}$ haloalkyl, —CN, SH, —$S(O)_2R^5$, —$COR^4$, —$CO_2R^4$, —$OC(O)R^5$, —$N(COR^4)_2$, —$NR^4R^7$ and —$CONR^4R^7$, —$NR^4COR^5$, $NR^4SO_2R^5$, $NR^4CONR^5R^7$ or $NR^4CO_2R^5$;
$R^3$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —$NR^4R^6$, —$C_{1-6}$alkyl$NR^4R^6$, —$C_{1-6}$alkyl$OR^6$, $CO_2R^6$, $O_2CR^6$, $COR^6$, $CON^4R^6$, $NR^4CO_2R^6$, $NR^4SO_2R^6$, $NR^4COR^6$, $OCONR^4R^6$, and $NR^4CONR^5R^6$;
   optionally and independently substituted with 1 to 3 substituents selected from the group consisting of —CN, hydroxy, halo, $C_{1-4}$ haloalkyl, $C_{1-4}$ alkoxy, $CO_2C_{1-4}$ alkyl, phenyl or naphthl; or
$R^3$ is morpholinyl, thiomorpholinyl, piperadinyl, piperazinyl, phenyl, pyridyl, pyrimidinyl, triazinyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl and indazolyl, independently and optionally substituted with 1 to 4 substituents selected from the group consisting of H, $C_{1-6}$ alkyl, $C_{3-6}$ cycloalkyl, $C_{1-4}$ alkoxy-$C_{1-4}$ alkyl, —$OR^4$, halo, $C_{1-6}$ haloalkyl, —CN, SH, —$S(O)_2R^5$, —$COR^4$, —$CO_2R^4$, —$OC(O)R^5$, —$N(COR^4)_2$, —$NR^4R^7$ and —$CONR^4R^7$, —$NR^4COR^5$, $NR^4SO_2R^5$, $NR^4CONR^5R^7$ or $NR^4CO_2R^5$;

Ar is selected from the group consisting of phenyl, indanyl, indenyl, pyridyl, pyrimidinyl, triazinyl, furanyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl, indazolyl, indolinyl, benzoxazolin-2-on-yl, benzodioxolanyl and benzodioxane, independently and optionally substituted with 1 to 4 substituents selected from the group consisting of H, $C_{1-6}$ alkyl, $C_{3-6}$ cycloalkyl, $C_{1-4}$ alkoxy-$C_{1-4}$ alkyl, —$OR^4$, halo, $C_{1-4}$ haloalkyl, —CN, —$NO_2$, SH, —$S(O)_2R^5$, —$COR^4$, —$CO_2R^4$, —$OC(O)R^5$, —$N(COR^4)_2$, —$NR^4R^7$ and —$CONR^4R^7$, —$NR^4COR^5$, $NR^4SO_2R^5$, $NR^4CONR^5R^7$, and $NR^4CO_2R^5$;

$R^4$, $R^5$ and $R^7$ are independently selected from the group consisting of H, $C_{1-6}$ alkyl, $C_{3-6}$ cycloalkyl, $C_{3-6}$ cycloalkyl-$C_{3-6}$ alkyl, $C_{1-2}$ alkoxy-$C_{1-4}$ alkyl and $C_{1-4}$ haloalkyl; and $R^6$ is selected from the group consisting of H, $C_{1-6}$ alkyl, $C_{3-6}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, phenyl and $C_{1-6}$ alkyl-phenyl.

2. A compound according to claim 1 wherein B is CH.

3. A compound according to claim 1 wherein B is CH and D is $CH_2$.

4. A compound according to claim 1 wherein B is CH and D is NH.

5. A compound according to claim 1 wherein $R^1$ is $C_{1-4}$ alkyl.

6. A compound according to claim 1 wherein $R^2$ is H or substituted or unsubsituted $C_{1-6}$ alkyl, morpholinyl, piperazinyl or phenyl.

7. A compound according to claim 1 wherein $R^3$ is H, halo, CN or hydroxy, substituted or unsubstituted $C_{1-6}$ alkyl, $C_{1-6}$ alkoxy, $C_{1-6}$ haloalkyl, —$NR^4R^6$ or $O_2CR^6$.

8. A compound according to claim 1 wherein $R^3$ is pyrimidinyl and pyridinyl.

9. A compound according to claim 1 wherein Ar is phenyl, pyridyl, pyrimidinyl, imidazolyl, thiazolyl, pyrrolidinyl, dihydroimidazolyl optionally substituted with 1 to 4 substituents selected from the group consisting of H, $C_{1-6}$ alkyl, —$OR^4$, halo, $C_{3-4}$ haloalkyl, —CN, —$NO_2$ or —$CO_2R^4$.

10. A compound according to claim 1 wherein $R^4$, $R^5$ and $R^7$ are independently H or $C_{1-6}$ alkyl.

11. A compound according to claim 1 wherein $R^6$ is H.

12. A compound according to claim 1 wherein $R^1$ is $C_{1-4}$ alkyl; $R^2$ is H or substituted or unsubsituted $C_{1-6}$alkyl, morpholinyl, piperazinyl or phenyl; $R^3$is H, halo, CN or hydroxy, substituted or unsubstituted $C_{1-6}$ alkyl, $C_{1-6}$ alkoxy, $C_{1-6}$ haloalkyl, —$NR^4R^6$ or $O_2CR^6$; Ar is phenyl, pyridyl, pyrimidinyl, imidazolyl, thiazolyl, pyrrolidinyl, dihydroimidazolyl optionally substituted with 1 to 4 substituents selected from the group consisting of H, $C_{1-6}$ alkyl, —$OR^4$, halo, $C_{1-4}$ haloalkyl, —CN, —$NO_2$ or —$CO_2R^4$; $R^4$, $R^5$ and $R^7$ are independently H or $C_{1-6}$ alkyl; and $R^6$ is H.

13. A compound according to claim 1 wherein B is CH; $R^1$ is $C_{1-4}$ alkyl; $R^2$ is H or substituted or unsubsituted $C_{1-6}$ alkyl, morpholinyl, piperazinyl or phenyl; $R^3$ is H, halo, CN or hydroxy, substituted or unsubstituted $C_{1-6}$ alkyl, $C_{1-6}$ alkoxy, $C_{1-6}$ haloalkyl, —$NR^4R^6$ or $O_2CR^6$; Ar is phenyl, pyridyl, pyrimidinyl, imidazolyl, thiazolyl, pyrrolidinyl, dihydroimidazolyl optionally substituted with 1 to 4 substituents selected from the group consisting of H, $C_{1-6}$ alkyl, —$OR^4$, halo, $C_{1-4}$ haloalkyl, —CN; —$NO_2$ or —$CO_2R^4$; $R^4$, $R^5$ and $R^7$ are independently H or $C_{1-6}$ alkyl; and $R^6$ is H.

14. [5-(4-Methoxybenzenesulfonyl)-2-methylpyrimidin-4-yl]-(2,4,6-trimethylphenyl)-amine; 4-[2-Methyl-4-(2,4,6-trimethylphenylamino)-pyrimidine-5-sulfonyl]-phenol; Acetic acid 4-[2-methyl-4-(2,4,6-trimethylphenylamino)-pyrimidine-5-sulfonyl]-phenyl ester; [5-(4-Benzyloxybenzenesulfonyl)-2-methylpyrimidin-4-yl-]-(2,4,6-trimethylphenyl)-amine; [5-(4-Benzyloxybenzenesulfonyl)-2-methylpyrimidin-4-yl]-(4-methoxy-2-methylphenyl)-amine; [5-(4-Benzyloxybenzenesulfonyl)-2-methylpyrimidin-4-yl]-(6-methoxy-2-methylpyridin-3-yl)-amine; [5-(3-Benzyloxybenzenesulfonyl)-2-methylpyrimidin-4-yl]-(2,4,6-trimethylphenyl)-amine; [5-(3-Benzyloxybenzenesulfonyl)-2-methoxypyrimidin-4-yl]-(2,4,6-trimethylphenyl)-amine; 5-(3-Benzyloxybenzenesulfonyl)-$N^2$, $N^2$-dimethyl-$N^4$-(2,4,6-trimethylphenyl)-pyrimidine-2,4-diamine; {5-[4-(2-Methoxybenzyloxy)-benzenesulfonyl]-2-methylpyrimidin-4-yl}-(2,4,6-trimethylphenyl)-amine; {5-[4-(3,5-Dimethoxybenzyloxy)-benzenesulfonyl]-2-methylpyrimidin-4-yl}-(2,4,6-trimethylphenyl)-amine; [5-(4-Benzyloxybenzenesulfonyl)-2-methylpyrimidin-4-yl]-(2,4-dimethoxyphenyl)-amine; 5-(4-Methoxyoxybenzenesulfonyl)-2-methyl-4-(2,4,6-trimethylbenzyl)-pyrimidine; 5-(4-Benzyloxybenzenesulfonyl)-2-methyl-4-(2,4,6-trimethylbenzyl)-pyrimidine; [5-(4-Fluorobenzenesulfonyl)-2-methylpyrimidin-4-yl]-(2,4,6-trimethylphenyl)-amine; [2-Methyl-5-(4morpholin-4-yl-benzenesulfonyl)-pyrimidin-4-yl]-(2,4,6-trimethylphenyl)-amine; {2-Methyl-5-[4-(4-methylpiperazin-1-yl)-benzenesulfonyl]-pyrimidin-4-yl}-(2,4,6-trimethylphenyl)-amine; [5-(4-Imidazol-1-yl-benzenesulfonyl)-2-methylpyrimidin-4-yl]-(2,4,6-trimethylphenyl)-amine; [2-Methyl-5-(4-pyrrolidin-1-yl-benzenesulfonyl)-pyrimidin-4-yl]-(2,4,6-trimethylphenyl)-amine; [5-(4-Benzylaminobenzenesulfonyl)-2-methylpyrimidin-4-yl]-(2,4,6-trimethylphenyl)-amine; {5-[4-(Benzylmethylamino)-benzenesulfonyl]-2-methylpyrimidin-4-yl}-(2,4,6-trimethylphenyl)-amine; 4-[2-Methyl-4-(2,4,6-trimethylphenylamino)-pyrimidine-5-sulfonyl]-benzonitrile; [2-Methyl-5-(toluene-4-sulfonyl)-pyrimidin-4yl]-(2,4,6-trimethylphenyl)-amine; [2-Methyl-5-(4-pyrimidin-5-yl-benzenesulfonyl)-pyrimidin-4-yl]-(2,4,6-trimethylphenyl)-amine; [2-Methyl-5-(4-pyrimidin-2-yl-benzenesulfonyl)-pyrimidin-4-yl]-(2,4,6-trimethylphenyl)-amine; [2-Methyl-5-(4-pyridin-4-yl-benzenesulfonyl)-pyrimidin-4-yl]-(2,4,6-trimethylphenyl)-amine; [2-Methyl-5-(4-pyridin-2-yl-benzenesulfonyl)-pyrimidin-4-yl]-(2,4,6-trimethylphenyl)-amine; [2-Methyl-5-(4-pyridin-3-yl-benzenesulfonyl)-pyrimidin-4-yl]-(2,4,6-trimethylphenyl)-amine; {5-[4-(4,5-Dihydro-1H-imidazol-2-yl)-6benzenesulfonyl]-2-methyl-pyrimidin-4-yl}-(2,4,6-trimethylphenyl)-amine; or {5-[4-(1H-Imidazol-2-yl)-benzenesulfonyl]-2-methyl-pyrimidin-4-yl}-(2,4,6-trimethylphenyl)-amine or pharmaceutically acceptable salts thereof.

15. A pharmaceutical composition comprising compound according to claim 1 and a pharmaceutically acceptable carrier.

16. A method of treating depression or anxiety comprising the administration of a compound of claim 1.

* * * * *